United States Patent [19]
Mann et al.

[11] Patent Number: 5,766,952
[45] Date of Patent: Jun. 16, 1998

[54] VAPOCHROMIC PLATINUM-COMPLEXES AND SALTS

[75] Inventors: Kent R. Mann, North Oaks; Charles A. Daws, Minneapolis, both of Minn.; Christopher L. Exstrom, Kearney, Nebr.; Daron E. Janzen, Minneapolis; Marie Pomije, Apple Valley, both of Minn.

[73] Assignee: Regents of The University of Minnesota, Minneapolis, Minn.

[21] Appl. No.: 686,279

[22] Filed: Jul. 25, 1996

[51] Int. Cl.$^6$ .................... G01N 31/22; G01N 31/00
[52] U.S. Cl. .................... 436/2; 436/126; 436/128; 436/129; 436/130; 436/131; 436/132; 436/139; 436/140; 436/141; 436/142; 436/164; 436/167; 436/166; 436/181; 436/183; 252/408.1
[58] Field of Search .................... 436/2, 126, 128–132, 436/139–142, 164, 167, 166, 181, 183; 252/408.1

[56] References Cited

U.S. PATENT DOCUMENTS

| | | |
|---|---|---|
| 3,197,493 | 7/1965 | Allison . |
| 3,458,542 | 7/1969 | Moore, Jr. et al. . |
| 4,102,201 | 7/1978 | Trine et al. . |
| 4,130,432 | 12/1978 | Wehner et al. . |
| 4,152,118 | 5/1979 | Elelr et al. . |
| 4,271,033 | 6/1981 | Gray et al. . |

(List continued on next page.)

OTHER PUBLICATIONS

Keller, H.J. et al. *Z. Naturforsch B* 1972, 27, 631–634.
F. Bonati et al *Gazz. Chim. Ital.* 1972, 102, 731–743.

(List continued on next page.)

*Primary Examiner*—Arlen Soderquist
*Attorney, Agent, or Firm*—Schwegman, Lundberg, Woessner & Kluth, P.A.

[57] ABSTRACT

The present invention relates to a process for indicating the presence of organic vapors comprising the steps of determining the color, absorption or emission spectra of a Pt—Pt double-complex salt of platinum or a neutral platinum complex in the absence of organic vapor, exposing said double-complex salt of platinum or a neutral platinum complex to a gaseous environment, determining the color, absorption or emission spectra of said double-complex salt of platinum or a neutral platinum complex after exposure to said gaseous environment, and comparing the color, absorption and/or emission spectra of said double-complex salt of platinum or a neutral platinum complex in the absence of organic vapor with the color, absorption and/or emission spectra of said double-complex salt of platinum or a neutral platinum complex after exposure to said gaseous environment to determine if there is a difference in the color, absorption and/or emission spectra. The double-complex salt is represented by the general formulas $[Pt(CN-C_6H_4\text{-alkyl group})_4][PtX_4]$ or $[Pt(phen)(CN-C_6H_4\text{-alkyl group})_2][PtX_4]$ of $[Pt(bpy)(CN-C_6H_4\text{-alkyl group})_2][PtX_4]$ and more preferably by the formulas $[Pt(CN-C_6H_4-C_nH_{2n+1})_4][Pt(CN)_4]$ or $[Pt(phen)(CN-C_6H_4\text{-alkyl group})_2][Pt(CN)_4]$ of $[Pt(bpy)(CN-C_6H_4\text{-alkyl group})_2][Pt(CN)_4]$, wherein n is a whole positive integer between 1 and 100. Still more preferably n is between 1 and 20. phen is 1,10-phenanthroline or an alkyl substituted phenanthroline. bpy is 2,2'-bipyridine or an alkyl substituted bipyridine. Other bidentate or tridentate amine ligands are also possible. The $PtX_4^{2-}$ group can also be $Pt(NO_2)_4^{2-}$, $Pt(Cl)_4^{2-}$, $Pt(Br)_4^{2-}$, $Pt(NCO)_4^{2-}$, $Pt(NCS)_4^{2-}$ or $Pt(oxalate)_2^{2-}$. For the bpy and phen complexes, the palladium analogs of $PtX_4^{2-}$ (ie. $PdX_4^{2-}$ are also possible). The neutral complexes are represented by the general formulas $Pt(CN-C_6H_4\text{-alkyl group})_2X_2$, and $Pt(CN-C_6H_4\text{-alkyl group})(C(Y)=NH-C_6H_4\text{-alkyl group})X_2$ wherein n is a whole positive integer between 1 and 100 and Y can be O-alkyl, NH-alkyl or $N(alkyl)_2$. Still more preferably n is between 1 and 20. The alkyl substituents may be different within the same complex. X is preferably $CN^-$, but any other negatively charged groups such as $NO_2^-$, $NCO^-$, $NCS^-$, $Cl^-$, $Br^-$, $I^-$, oxalate, etc. may also be used. The two $X^-$ groups are not necessarily the same.

40 Claims, 8 Drawing Sheets

U.S. PATENT DOCUMENTS

| | | | |
|---|---|---|---|
| 4,350,660 | 9/1982 | Robinson et al. | 422/90 |
| 4,381,922 | 5/1983 | Frey et al. | 422/98 |
| 4,442,297 | 4/1984 | Hill et al. | 549/206 |
| 4,452,774 | 6/1984 | Jones et al. | 424/1.1 |
| 4,710,476 | 12/1987 | Ellis et al. | 436/172 |
| 4,826,774 | 5/1989 | Nagel | 436/106 |
| 4,834,909 | 5/1989 | Nagel | 252/408.1 |
| 5,445,795 | 8/1995 | Lancaster et al. | 422/86 |

OTHER PUBLICATIONS

H.J. Keller et al. *J. Organomet. Chem.* 1975, 102, 119–122.

H.J. Keller et al. *Inorg. Nucl. Chem. Lett.* 1975, 11, 765–768.

H.J. Keller et al. *Z. Naturforsch B* 1976, 31B, 565–568.

S.D. Cuatecontzi et al. *J. Chem. Res. S* 1977, 137.

Y. Yamamoto et al. *Chem. Lett.* 1985, 201–204.

S.S. Kamath et al. *Inorg. Chim. Acta* 1989, 166, 91–98.

V.M. Miskowski et al. *Inorg. Chem.* 1991, 30, 4446–4452.

S.M. Angel et al. *Proc. SPIE–Int. Soc. Opt. Eng.* 1992, 1587, 86–95.

C. Vogler et al. *J. Organomet. Chem.* 1992, 436, 367–378.

T. Kaharu et al. *J. Mater. Chem.* 1994, 4, 859–865.

C.L. Exstrom et al. *Chem. Mater.* 1995, 7, 15–17.

S.-W. Zhang et al. *J. Organmet. Chem.* 1995, 489, C62–C64.

C.J. Murphy et al. *Proc. SPIE–Int. Soc. Opt. Eng.* 1995, 2388, 266–272.

C.A. Daws et al. *Chem. Mater.* 1997, 9, 363–368.

Flavio Bonati, et al., "New Isocyanide Complexes of Platinum(II)", *J. Organomet. Chem.*, 24, 251–256, (1970).

Flavio Bonati, et al., "Recent Advances in the Chemistry of Isocyanide Complexes", *Inorganica Chimica Acta*, 9, 95–112, (1974).

J. F. Giuliani, et al., "Reversible Optical Waveguide Sensor for Ammonia Vapors", *Optics Letters*, 8, 54–56, (1983).

E. E. Hardy, et al., "Coated Optical Guides for Spectrophotometry of Chemical Reactions", *Nature*, 257, 666–667, (1975).

Huseyin Isci, et al., "Anion–Cation Interaction in Tetrakis(alkyl isocyanide)platinum(II) Tetracyanoplatinate(II) Double Complexes in the Solid State and in Solution", *Inorganic Chemistry*, 13, 1175–1180, (1974).

Huseyin Isci, et al., "Electronic Structure and Spectra of Square–Planar Alkyl Isocyanide Complexes", *Inorganic Chem.*, 14, 913–918, (1975).

W. Roy Mason, II, et al., "Electronic Structures of Square–Planar Complexes", *J. Amer. Chem. Soc.*, 90, 5721–5729, (1968).

Andrew Mills, et al., "Equilibrium Studies on Colorimetric Plastic Film Sensors for Carbon Dioxide", *Anal. Chem.*, 64, 1383–1389, (1992).

Jorg Reinbold, et al., "Inclusion of Organic Vapours by Crystalline Hosts. Chemical–Sensitive Coatings for Sensor Applications", *Sensors and Actuators B*, 18–19, 77–81, (1994).

K. D. Schierbaum, "Application of Organic Supramolecular and Polymeric Compounds for Chemical Sensors", *Sensors and Actuators B*, 18–19, 71–76, (1994).

B. Singleton, et al., "Metal Isocyanide Complexes", *Adv. Organomet. Chem.*, 22, 209–238, (1983).

Mark L. Winzenburg, et al., "Rhodium(I) and Platinum(II) Complexes with Chelating Bidentate Isonitrile Ligands", *J. of Organometallic Chem.*, 249, 415–428, (1983).

5,766,952

VAPOCHROMIC PLATINUM-COMPLEXES AND SALTS

BACKGROUND OF THE INVENTION

1. Field of the Invention

This invention relates to articles comprising transition metal-containing double-complex salts and neutral complexes. These salts and neutral complexes exhibit vapochromic properties and are useful in chemical, physical, and environmental monitoring applications.

2. Background of the Art

Historically, complexes containing isonitrile ligands have been limited to those containing the few commercially available isonitriles like t-BuNC, PhNC, or the readily synthesized and purified isonitriles like MeNC, EtPhNC, MeOPhNC, MePhNC wherein t-Bu=tertiary butyl, Ph=phenyl, Et=ethyl, and Me=methyl. For review see: Bonati, F.; Minghetti, G. Inorg. Chim. Acta 1974, 9, 95–112. More 'exotic' isonitriles have been studied by (Winzenburg M. L.; Kargol, J. A.; Angelici, R. J. J. Organomet. Chem 1983, 249, 415–428).

Salts of the type [L$_4$M][M'X$_4$] are known as double complex salts, i.e., the salt is composed of two metal-containing complex ions. Salts where L is often amnine or isonitrile, X is a halide or cyanide, and both M and M' are platinum have been known for many years. A review of metal isocyanide complexes is available in Singleton, E., Oosthuizen, H. E. Adv. Organomet. Chem. 1983, 22, 209–238. Both the cation and anion comprising these complexes have square-planar geometries and often assume structures in which the ions form mixed stacks; the resulting metal-metal interactions causing these solids to be intensely colored despite the fact that the component ions absorb below 350 nanometers (Bonati, F., Minghetti, G., J. Organomet. Chem. 1970, 24, 251; Isci and Mason, Inorg. Chem 1975, 14, 913; Mason, W. R., Gray, H. B., J Am. Chem Soc. 1968, 90, 5721). A study of the optical properties of these complexes is reported by Isci and Mason, (Inorg. Chem. 1974, 13, 1175–1180).

Simple salts having cations of the type [(RNC)$_4$]M$^+$ where M includes radioactive isotopes of Rh(I) and Ni(II), Pd(II), or Pt(II) are described in U.S. Pat. No. 4,452,774 for use as diagnostic agents for labeling living cells. U.S. Pat. No. 4,271,033 describes binucleating biisocyanide complexes of Rh, Pt, Pd, Ni useful as catalysts. Isonitrile or isocyanide complexes of copper, described in U.S. Pat. No. 3,197,493, are useful as intermediates in the preparation of isonitriles.

U.S. Pat. No. 4,130,432 claims alkyl tin tetracyanometallates as biocides. Double salts of tetracyanoaurate useful for plating gold alloys are described in U.S. Pat. No. 3,458,542. The use of transition metals in sensors is known in the art; transition metal complexes used have predominantly been phthalocyanine or porphyrin derivatives as seen, for example, in U.S. Pat. No. 4,381,922 and U.S. Pat. No. 4,350,660.

U.S. Pat. No. 4,152,118 which claims a phosphine copper complex which functions as a sulfur dioxide indicator. U.S. Pat. No. 4,442,297 describes manganese complexes which coordinate hydrogen, carbon monoxide, oxygen, sulfur dioxide, and alkenes and can be used as indicators or gas separators.

Methods have been devised to chemically trap and analyze vapors as taught in U.S. Pat. No. 4,102,201; however, such methods do not allow for immediate (real time) indication of organic vapors. Sensing of gases using optical waveguide gas sensors was first reported in 1975 by Hardy, David, Kapany, and Unterleitner, (Nature 1975, 257, 666–667). State of the art optical waveguide sensors often utilize chemically reactive dyes which, unfortunately, often have limited shelf life, may undergo irreversible chemical changes and are chemically specific as described by Giuliani, Wohltjen, and Jarvis. (Optics Letters 1983, 8, 54–56, and references cited therein).

Indication of chemical vapors by photoluminescent semiconductors has been shown where emission spectra are altered by contact of the vapors with emitting surfaces, as in U.S. Pat. No. 4,710,476.

U.S. Pat. No. 4,826,774 provides an article comprising a vapochromic transition metal double-complex salt comprising four aryl isonitrile ligands, at least one of which, and preferably all, contains a long chain aliphatic group, the salt having two metal-containing complex ions, the cation being a tetrakis isonitrile ligand-containing platinum ion and the anion being a tetracyanopalladate ion. Both the cation and anion in the double-complex salts have a d$^8$ electronic configuration (8 electrons in the "d" orbitals) or are capable of forming a square planar configuration. The complex salts are water and air stable. The mixed transition metal double-complex salts of that invention are vapochromic and highly colored as well as fluorescent in the visible spectrum; thus, visual as well as instrumental and optical monitoring of vapors is possible. Those complex salts are described as useful for personal and badge monitors, threshold monitors, optical waveguide sensors, chemical field effect transistors, and in related monitoring applications, even when the monitors are wet or subjected to moisture. In all cases, at least a portion of the solid complex is not overcoated by any other material.

U.S. Pat. No. 4,834,909 describes thermochromic double-complex salts comprising square planar transition metal double complex salts which contain isonitrile ligands derivatized with long chain aliphatic groups. Amongst the complex salts are Pt—Pt double complex salts.

SUMMARY OF THE INVENTION

The present invention relates to a process for indicating the presence of organic vapors comprising the steps of determining the color, absorption or emission spectra of a Pt—Pt double-complex salt of platinum or a neutral platinum complex in the absence of organic vapor, exposing said double-complex salt of platinum or neutral platinum complex to a gaseous environment, determining the color, absorption or emission spectra of said double-complex salt of platinum or neutral platinum complex after exposure to said gaseous environment, and comparing the color, absorption and/or emission spectra of said double-complex salt of platinum or neutral platinum complex in the absence of organic vapor with the color, absorption and/or emission spectra of said double-complex salt of platinum or neutral platinum complex after exposure to said gaseous environment to determine if there is a difference in the color, absorption and/or emission spectra.

The double-complex salts (FIG. 1) are represented by the general formulas a) [Pt(CN—C$_6$H$_4$-alkyl group)$_4$][PtX$_4$], b) [Pt(phen)(CN—C$_6$H$_4$-alkyl group)$_2$][PtX$_4$] or c) [Pt(bpy)(CN—C$_6$H$_4$-alkyl group)$_2$][PtX$_4$] and more preferably by the formulas d) [Pt(CN—C$_6$H$_4$—C$_n$H$_{2n+1}$)$_4$][Pt(CN)$_4$], e) [Pt(phen)(CN—C$_6$H$_4$-alkyl group)$_2$][Pt(CN)$_4$] or f) [Pt(bpy)(CN—C$_6$H$_4$-alkyl group)$_2$][Pt(CN)$_4$], wherein n is a whole positive integer between 1 and 100. Still more preferably n is between 1 and 20. Phen is 1,10-phenanthroline or an alkyl substituted phenanthroline, bpy is 2,2'-bipyridine or an alkyl substituted bipyridine. Other bidentate or tridentate amine ligands are also possible. The $PtX_4^{2-}$ group can also be $Pt(NO_2)_4^{2-}$, $Pt(Cl)_4^{2-}$, $Pt(Br)_4^{2-}$, $Pt(NCO)_4^{2-}$, $Pt(NCS)_4^{2-}$ or $Pt(oxalate)_2^{2-}$. For the bpy and phen complexes, the palladium analogs of $PtX_4^{2-}$ (i.e., $PdX_4^{2-}$) are also possible. The compounds of formulae a), b) and c) where each alkyl group has three or more carbons or X is other than —CN are novel compounds.

Neutral platinum complexes are defined according to the present invention as platinum complexed by four ligands wherein two ligands are negatively charged groups selected from the group consisting of $CN^-$, $NO_2^-$, $NCO^-$, $NCS^-$, $Cl^-$, $Br^-$, $I^-$, and oxalate and the remaining two ligands are selected from the group of at least one and at most two arylisonitrile groups, and a Fisher carbene (i.e., (C(Y)=NH—$C_6H_4$-alkyl group) wherein Y can be O-alkyl, NH-alkyl or $N(alkyl)_2$. The neutral complexes are represented by the general formulas Pt(CN—$C_6H_4$-alkyl group)$_2X_2$, Pt(CN—$C_6H_4$-alkyl group)(C(Y)=NH—$C_6H_4$-alkyl group)$X_2$ wherein n is a whole positive integer between 1 and 100 and Y can be O-alkyl, NH-alkyl or $N(alkyl)_2$. Still more preferably n is between 1 and 20. The alkyl substituents may be different within the same complex. X is preferably $CN^-$, but any other negatively charged group such as $NO_2^-$, $NCO^-$, $NCS^-$, $Cl^-$, $Br^-$, $I^-$, oxalate, etc. may also be used. The two $X^-$ groups are not necessarily the same. These neutral platinum complexes are novel compounds.

DETAILED DESCRIPTION OF THE INVENTION

Figure 1:
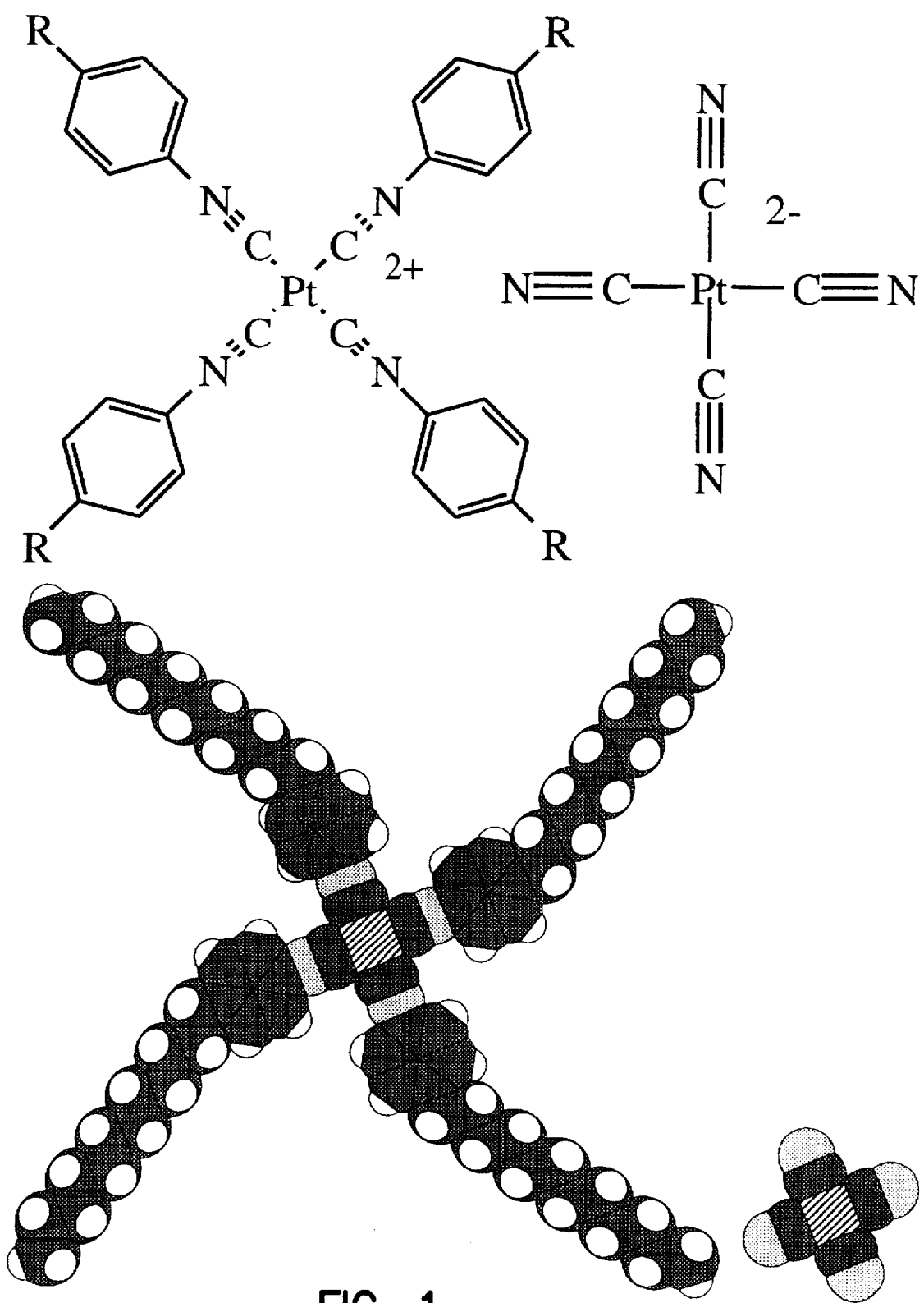
FIG. 1 is a representation of space-filling models of [Pt(CN—$C_6H_4$—$C_{10}H_{21}$)$_4$][Pt(CN)$_4$].

The present invention relates to a process for indicating the presence of organic vapors comprising the steps of: determining a first color, absorption or emission spectra of a Pt—Pt double-complex salt of platinum or a neutral platinum complex in the absence of organic vapor, exposing said double-complex salt of platinum or a neutral platinum complex to a gaseous environment, determining a second color, absorption or emission spectra of said double-complex salt of platinum or a neutral platinum complex after exposure to said gaseous environment, and comparing the color, absorption or emission spectra of said double-complex salt of platinum or a neutral platinum complex in the absence of organic vapor (the first color, absorption or emission spectra), with the visible, infrared and/or emission spectra of said double-complex salt of platinum or a neutral platinum complex after exposure to said gaseous environment (the second color, absorption or emission spectra), to determine if there is a difference in the color, absorption or emission spectra. The spectra may be obtained in the visible infrared or near infrared regions.

As noted above, neutral platinum complexes are defined according to the present invention as platinum complexed by four ligands wherein two ligands are negatively charged groups selected from the group consisting of $CN^-$, $NO_2^-$, $NCO^-$, $NCS^-$, $Cl^-$, $Br^-$, $I^-$, and oxalate and the remaining two ligands are selected from the group of at least one and at most two arylisonitrile groups, and a Fisher carbene (i.e., (C(Y)=NH—$C_6H_4$-alkyl group) wherein Y can be O-alkyl, NH-alkyl or $N(alkyl)_2$. The neutral complexes are represented by the general formulas Pt(CN—$C_6H_4$-alkyl group)$_2X_2$, Pt(CN—$C_6H_4$-alkyl group)(C(Y)=NH—$C_6H_4$-alkyl group)$X_2$ wherein n is a whole positive integer between 1 and 100 and Y can be O-alkyl, NH-alkyl or $N(alkyl)_2$. Still more preferably n is between 1 and 20. The alkyl substituents may be different within the same complex. X is preferably $CN^-$, but any other negatively charged group such as $NO_2^-$, $NCO^-$, $NCS^-$, $Cl^-$, $Br^-$, $I^-$, oxalate, etc. may also be used. The two $X^-$ groups are not necessarily the same. Although the $CN^-$ and $NO_2^-$ anions are primarily used in the examples, the other anions may of course be prepared in the final compounds merely by the appropriate selection of reagents. Yields may vary slightly or significantly because of solubility differences in the various steps along the reaction path, but the compounds with different anions can otherwise be made according to the synthetic procedures used for the cyano and $NO_2^-$ anions.

The double-complex salt is represented by the general formulas [Pt(CN—$C_6H_4$-alkyl group)$_4$][PX$_4$] or [Pt(Phen)(CN—$C_6H_4$-alkyl group)$_2$][PtX$_4$] of [Pt(bpy)(CN—$C_6H_4$-alkyl group)$_2$][PtX$_4$] and more preferably by the formulas [Pt(CN—$C_6H_4$—$C_nH_{2n+1}$)$_4$][Pt(CN)$_4$] or [Pt(phen)(CN—$C_6H_4$-alkyl group)$_2$][Pt(CN)$_4$] of [Pt(bpy)(CN—$C_6H_4$-alkyl group)$_2$][Pt(CN)$_4$], wherein n is a whole positive integer between 1 and 100. Still more preferably n is between 1 and 20. Phen is 1,10-phenanthroline or an alkyl substituted phenanthroline, bpy is 2,2'-bipyridine or an alkyl substituted bipyridine.

The term alkyl group in the practice of the present invention shall mean both alkyl moiety substituents of the general formula $C_nH_{2n+1}$ and alkyl groups in which one or more hydrogens have been replaced with substituent groups such as halogen (e.g., Cl, Br, I, and F, including up to perfluorinated alkyl), hydroxy, cyano, nitro, alkoxy, deuterium and the like. Additional substituent groups which are specifically contemplated in the practice of the present invention include, for example, p-CN—$C_6H_4$—R, wherein R may be hydrogen, thio, thioalkyl, deuterium, and alkyl groups (e.g., methyl, ethyl, propyl, isopropyl, butyl, sec-butyl, t-butyl, and cycloalkyl such as cyclohexyl, cyclopentyl, cyclobutyl and cyclopropyl. These compounds are synthesizable by appropriate substitution of reactants in the generic synthetic procedures provided herein. Where the term alkyl group is used, such substitution and non-substitution is intended to be included by the term. Where the term "alkyl moiety" is used, no replacement of hydrogens on the alkyl chain is allowed.

The synthesis, characterization and Vis-NIR-IR vapochromic/spectroscopic studies are reported for isonitrile compounds of the form [Pt(arylisonitrile)$_4$][Pt(CN)$_4$] (where arylisonitrile is p-CN—$C_6H_4$—$C_nH_{2n+1}$; n=1, 6, 10, 12, 14). The dark blue, solid materials change color in the NIR (near infrared) spectral region upon exposure to the ambient room temperature vapor pressure of volatile organic compounds (VOCs). At room temperature the Pt—Pt compounds exhibit strong solid state absorption and emission bands in the NIR region of the spectrum that are red shifted from similar bands in the Pt Pd analogs; (n=1, $\lambda_{max}$ abs=744, $\lambda_{max}$ emit=958; n=6, $\lambda_{max}$ abs=84 1, $\lambda_{max}$ emit=910; n=10, $\lambda_{max}$ abs=746, $\lambda_{max}$ emit=972; n=12, $\lambda_{max}$ abs=764, $\lambda_{max}$ emit= 912; n=14, $\lambda_{max}$ abs=690, $\lambda_{max}$ emit=876 nm). The positions of these bands depend on the number of carbons in the alkyl group. The absorption and emission bands for the solid material (n=10 compound) also exhibit a substantial red shift upon cooling to 77K ($\lambda_{max}$ abs (293K)=746; $\lambda_{max}$ emit (293K) =932; $\lambda_{max}$ abs (77K)=846 ; $\lambda_{max}$ emit (77K)=1094 nm) that is consistent with an alternating cation-anion stacked structure. Qualitatively, the vapochromicity of the compounds follows the ordering n=10>>6>1–12>14. The shifts observed for $\lambda_{max}$ abs (at 293K) are on the order of 700 cm$^{-1}$ and are 2–3 times greater than those exhibited by the Pt Pd analog compounds of U.S. Pat. No. 4,826,774 under identical conditions. The n=10 compound is the most responsive; the positions of the Vis-NIR band in the presence of several solvent vapors are as follow: none, 746 nm; methanol, 757; ethanol, 782; iso-propanol, 782; diethyl ether, 787; acetonitrile, 809; hexanes, 775; acetone, 800; benzene, 801; dichloromethane, 811; chloroform, 837. No response was observed for water vapor. IR studies of films of the n=10 compound on an ATR crystal show that the sorption of VOC by the solid causes no change in the v(RCN) isonitrile stretching frequency but in some cases a substantial shift (0–15 cm$^{-1}$) in v(CN) of the cyanide stretch is observed. When the n=10 compound contacts VOCs capable of H-bonding with the Pt(CN)$_4^{2-}$ anion, two cyanide stretches are observed. All the spectroscopic data suggest that the VOC penetrates the solid and interacts with the linear chain chromophore to cause the spectral shifts in the Vis-NIR-IR spectral regions. The vapochromic shifts are suggested to be due to dipole-dipole and/or H-bonding interactions between the Pt(CN)$_4^{2-}$ anion and polar VOCs; for non-polar VOCs, lypophilic interactions between the VOC and the isonitrile ligands that cause no change in the v(CN) stretching region, must cause the NIR vapochromism observed. The absence of a vapochromic response for water vapor is suggested to arise from hydrophobic blocking of the water at the solid/gas interface.

The development of rugged, chemical sensor materials has received increasing attention (See for example the description of the "Electronic Nose": ((a) Persaud, K., Dodd, G. H. *Nature (London)*, 1982, 299, 352; (b) Shurmer, H. V. *Anal. Proc. Inc. Anal. Comm.* 1994, 31 39) with the growing need to detect volatile organic compounds (VOCs) in the environment and the workplace (The U. S. EPA Environmental Technology Initiative for FY 1994 includes monitoring VOCs as a critical need). Of particular interest are materials that show dramatic and reversible color changes in the visible or near-infrared (NIR) spectral regions upon exposure to VOCs. Ideally, such materials would not only detect VOCs below the part per million (ppm) level but they would also show a unique response for each VOC. Responsive compounds that report in the NIR region may be particularly promising because of intrinsic low level background interferences ((a) Soper, S. A.; Mattingly, Q. L.; Vegunta, P. *Anal. Chem.*, 1993, 65, 740; (b) Williams, R. J.; Lipowska, M.; Patonay, G.; Strekowski, L. *Anal. Chem.*, 1993, 65, 601, (c) Imasaka, T. Yoshitake, A.; Ishibashl, N. *Anal. Chem.*, 1984, 56, 1077; (d) Ishibashl, N.; Imasaka, T. Sauda, K. *Anal. Chem.*, 1986, 58, 2649; (e) Imasaka, T. Ishibashi, N. *Anal. Chem.*, 1991), 62, 363A).

Square-planar d$^8$ complexes that stack in the solid state (The prototype is [Pt(H$_3$)$_4$][PtCl$_4$], Magnus' green salt; (a) Magnus, G. *Pogg. Ann.*, 1828, 11, 242; (b) Atoji, M.; Richardson, J. W.; Rundle, R. E., *J. Amer. Chem. Soc.*, 1957, 79, 3017. Also see (c) Connely, N. G., Crossley, J. G.; Orpen, A. G.; Salter, H. J *Chem. Soc. Chem.* Commun. 1992, 1564) show promise as sensor materials because they are robust and spectroscopically sensitive to VOC presence (Exstrom, C. L.; Sowa, J. R. Jr.; Daws, C. A.; Janzen, D.; Moore, G. A.; Stewart, F.F., Mann, K. R. *Chem. Mater.* 1995, 7, 15). It is well established that the electronic structure of square-planar Pt(II) compounds is often perturbed in the solid-state (Gliemann, G., Yersin, H. *Struct Bonding* 1985, 62, 87). Crystallization in linear-chain stacks gives rise to Pt—Pt interactions that significantly lower the metal-to-ligand-charge transfer (MLCT) or d-sigma* to p-sigma energy (Miskowski, V. M.; Houlding, V. H. *Inorg. Chem.* 1991, 30, 4446). Additional absorption shifts have been reported when insoluble double-complex salts ([PtL$_4$] [PtX$_4$]) of Pt(II) are suspended in water or organic solvents (For ionic stacks see: Little, W. A.; Lorentz, R. *Inorg. Chem. Acta*, 1976, 18, 273. For example, [Pt(bipy)$_2$ [Pt(CN)$_4$] (bipy=2,2'-bipyridine) has an absorption $\lambda_{max}$ of 485 nm in aqueous suspension compared to 514 nm (dry); in an EtOH/ benzene suspension, the absorption maximum for [Pt(phen) $_2$][Pt(C$_2$O$_4$)$_2$] (phen=1,10-phenanthroline) shifts from 537 (dry) to 575 nm.). These shifts indicate that the solid state d$^8$ stacked structure can be perturbed by interactions with interstitial solvent molecules.

We recently reported (Exstrom, C. L.; Sowa, J. R. Jr.; Daws, C. A.; Janzen, D.; Moore, G. A., Stewart, F. F.; and Mann, K. R.; *Chem. Mater.*, 1995, 7, 15) that significant $\lambda_{max}$ shifts in absorption and emission for [Pt(arylisonitrile) $_4$][Pd(CN)$_4$] (where arylisonitrile=p-CN—$C_6H_4C_nH_{2n+1}$ (n=6, 10, 12, 14) occur upon exposure to VOC vapors. The size mismatch between the cation and anion complexes apparently produces an open structure that can reversibly sorb VOCs. Incorporation of the VOC into the lattice perturbs the cation-anion stacking structure and causes a shift in the absorption maximum, but does not significantly disrupt the crystallinity of the compounds. A striking color change (from pink to blue) was observed for the n=10 Pt-Pd double-complex salt upon exposure to VOCs.

In this patent we describe the synthesis, characterization, and spectroscopic studies of the homometallic analog complexes [Pt(arylisonitrile)$_4$][Pt(CN)$_4$] (where arylisonitrile=p-CN—C$_6$H$_4$—C$_n$H$_{2n+1}$; n=1, 6, 10, 12, 14). Substitution of Pt(CN)$_4^{2-}$ for the Pd(CN)$_4^{2-}$ anion enhances the stability of the compounds, lowers the absorption and emission band energies into the NIR spectral region and gives compounds that show greater "vapochromic" shifts than their [Pd(CN)$_4$]$^{2-}$ analogs.

EXAMPLES

Ligand Synthesis and Characterization.

p-CH$_3$—C$_6$H$_4$—NC was prepared as reported by Ugi and Meyer (Synthesis of isonitriles: (a) Ugi, I.; Meyer, R.; McKusick, B. C.; Webster, O. W. *Org. Synth.* 1961, 41, 101. All other aryl isonitriles were prepared from the corresponding amines via the formamide compounds either by a modification of this procedure or that reported by Bringmann and Schneider (Synthesis of isonitriles, Bringmann, G.; Schneider, S. *Angew. Chem. Int. Ed. Engl.* 1983,23, 139).

p-C$_n$H$_{2n+1}$—C$_6$H$_4$—NHCHO (n=6, 10, 12, 14). The synthesis of p-C$_{10}$H$_{21}$—C$_6$H$_4$—NHCHO is given as an example. All other formamides were prepared in an analogous manner. A mixture of p-C$_{10}$H$_{21}$—C$_6$H$_4$—NH$_2$) (5.72 g, 24.5 mmol), 90% formic acid (15 ml), and toluene (100 mL) was stirred and refluxed under a condensor attached to a Dean-Stark water separator for 16 h. As the reaction progressed, the solution color turned from a dark red-brown to pale yellow. Cooling the mixture to 0° C. afforded white flakes of p-C$_{10}$H$_{21}$—C$_6$H$_4$—NHCHO (4.91 g, 77%), which were separated from the mixture by filtration. To obtain a second crop of formamide, the solvent was removed from the filtrate under vacuum. The residue was dissolved in a minimum of pentane and cooled to 0° C. to give an additional 1.02 g of p-C$_{10}$H$_{21}$—C$_6$H$_4$—NHCHO.

p-C$_6$H$_{13}$—C$_6$H$_4$—NHCHO. Yield=67%; $^1$H NMR (CDCl$_3$) δ7.13 (m, 4 H, Ph), 2.57 (m, 2 H, (CH$_2$)Ph), 1.58 (m, 2 H, (CH$_2$)CH$_2$Ph), 1.29 (m, 6 H, CH$_2$), 0.87 (t, 3 H, CH$_3$); IR (CH$_2$Cl$_2$) v(CO) (cm$^{-1}$) 1693 s.

p-C$_{10}$H$_{21}$C$_6$H$_4$—NHCHO. Yield=95%; $^1$H NMR (CDCl$_3$) δ7.13 (m, 4 H, Ph), 2.56 (m, 2 H, (CH$_2$)Ph), 1.57 (m, 2 H, (CH$_2$)CH$_2$Ph), 1.25 (m, 14 H, CH$_2$), 0.87 (t, 3 H, CH$_3$); IR (CH$_2$Cl$_2$) v(CO) (cm$^{-1}$) 1696 s.

p-C$_{12}$H$_{25}$—C$_6$H$_4$—NHCHO. Yield=69%. $^1$H NMR (CDCl$_3$) δ7.20 (m, 4 H, Ph), 2.57 (t, 2 H, (CH$_2$)Ph), 1.55 (m, 2 H, (CH$_2$)CH$_2$Ph), 1.25 (m, 14 H, CH$_2$), 0.87 (t, 3 H, CH$_3$); IR (CH$_2$Cl$_2$) v(CO) (cm$^{-1}$) 1698 s.

p-C$_{14}$H$_{29}$—C$_6$H$_4$—NHCHO. Yield=85%; $^1$H NMR (CDCl$_3$) δ7.15 (m, 4 H, Ph), 2.56 (t, 2 H, (CH$_2$)Ph), 1.57 (m, 2 H, (CH$_2$)CH$_2$Ph), 1.25 (m, 22 H, CH$_2$), 0.87 (t, 3 H, CH$_3$); IR (CH$_2$Cl$_2$) v(CO) (cm$^{-1}$) 1692 s.

p-C$_n$H$_{2n+1}$—C$_6$H$_4$—NC (n=6, 10). These compounds were prepared by a modification of the method reported by Ugi and Meyer (vide supra). The synthesis of p-C$_{10}$H$_{21}$—C$_6$H$_4$—NC is given as an example. The hexyl substituted isonitrile (n=6) was prepared in an analogous manner. Triethylamine was dried over 3 Å Molecular Sieves and passed through a column of activated neutral alumina before use. A mixture of p-C$_{10}$H$_{21}$—C$_6$H$_4$—NHCHO (7.05 g, 27.0 mmol), triethylamine (35 mL, 250 mmol), and CH$_2$Cl$_2$ (100 ml) was cooled to 0° C. in an icewater bath. With stirring, POCl$_3$ (5.0 mL, 54 mmol) was added to the mixture dropwise over a 10-minute period. The mixture was stirred at 0° C. for 1 h, during which the solution color gradually turned from pale yellow to orange-brown. The ice-water bath was removed and a 25% (w/w) aqueous sodium acetate solution (100 mL) was added to the reaction mixture and stirred for 30 min. The organic layer was removed, washed three times with a saturated NaCl solution (75 mL ea.), and dried with anhydrous CaCl$_2$. The solvent was removed by rotary evaporation, and the remaining solid was purified by column chromatography (silica gel column), using a 1:9 mixture of ethyl acetate/CH$_2$Cl$_2$ as the mobile phase. Recrystallization from ethanol afforded white needle-like crystals of p-C$_{10}$H$_{21}$—C$_6$H$_4$—NC (4.03 g, 61%). $^1$H NMR(CD$_2$Cl$_2$) δ7.28 (d, 2 H, Ph), 7.20 (d, Ph), 2.62 (t, 2 H, (CH$_2$)Ph), 1.58 (m, 2 H, (CH$_2$)CH$_2$Ph), 1.26 (m, 14 H, CH$_2$),0.88 (t, 3 H, CH$_3$); IR (CH$_2$Cl$_2$) v(NC) (cm$^{-1}$) 2128 vs.

p-C$_6$H$_{13}$—C$_6$H$_4$—NC. After column chromatography, this compound was isolated as a pale-green liquid (71% yield). $^1$H NMR (CD$_2$Cl$_2$) δ7.29 (d, 2 H, Ph), 7.20 (d, 2 H, Ph), 2.62 (t, 2 H, (CH$_2$)Ph), 1.59 (m, 2 H, (CH$_2$)CH$_2$Ph), 1.31 (m, 6 H, CH$_2$), 0.88 (t, 3 H, CH$_3$); IR (CH$_2$Cl$_2$) v(NC) (cm$^{-1}$) 2130 vs.

p-C$_n$H$_{2n+1}$—C$_6$H$_4$—NC (n=12, 14). These compounds were prepared by a modification of the procedure reported by Bringman and Schneider (vide supra). The synthesis of pC$_{12}$H$_{25}$—C$_6$H$_4$—NC is given as an example. The other isonitrile was prepared in an analogous manner. Triethylamine was dried over 3 Å Molecular Sieves and passed through a column of activated neutral alumina before use. A mixture of p-C$_{12}$H$_{25}$—C$_6$H$_4$—NHCHO (10.0 g, 34.5 mmol), triphenylphosphine (9.05 g, 34.5 mmol), and CH$_2$Cl$_2$ (250 mL) was cooled to 0° C. in an ice-water bath. To this mixture, an ice-cold solution of C$_2$Br$_2$Cl$_4$ (22.5 g, 69.0 mmol) in triethylamine (19.2 mL, 13.8 mmol) was added with stirring. The reaction mixture was stirred for 15 min at -10° C., then the ice bath was removed and the mixture was stirred at room temperature for 1 h. After cooling to 0° C., the mixture was filtered, and the filtrate was washed with H$_2$O (3×50 mL) and saturated aqueous NaCl (2×50 mL) and dried over anhydrous MgSO$_4$. The solvent was removed by rotary evaporation, leaving an oily residue. This was dissolved in warm ethanol (200 mL) and activated carbon was added with stirring. The solution was passed through a Celite column to remove the carbon and cooled to -10° C. to afford white crystals of p-Cl$_2$H$_{25}$—C$_6$H$_4$NC (68%). $^1$H NMR (CD$_2$Cl$_2$) δ7.29 (d, 2 H, Ph), 7.20 (d, 2 H, Ph), 2.62 (t, 2 H, (CH$_2$)Ph), 1.58 (m, 2 H, (CH$_2$)CH$_2$Ph), 1.26 (m, 18 H, CH$_2$), 0.88 (t, 3 H, CH$_3$); IR (CH$_2$Cl$_2$) v(NC) (cm$^{-1}$) 2130 s.

p-C$_{14}$H$_{29}$—C$_6$H$_4$—NC. Yield=40%; $^1$H NMR (CD$_2$Cl$_2$) δ7.29 (d, 2 H, Ph), 7.20 (d, 2 H, Ph), 2.61 (t, 2 H, (CH$_2$)Ph), 1.58 (m, 2 H, (CH$_2$)CH$_2$Ph), 1.26 (m, 22 H, CH$_2$), 0.88 (t, 3 H, CH$_3$); IR (CH$_2$C$_{12}$) v(NC) (cm$^{-1}$) 2127 s.

Synthesis and Characterization of Metal Complexes [Pt (p-CN—C$_6$H$_4$—C$_n$H$_{2n+1}$)$_4$][Pt(X)$_4$] where X=CN or NO$_2$.

Double-complex salts were prepared by a modificiation of the method reported by Nagel, C. C., U.S. Pat. No. 4,834, 909; (b) Nagel, C. C., U.S. Pat. No. 4,826,774). Syntheses were performed under either argon or N$_2$ atmospheres, using standard Schlenk techniques. Acetonitrile was distilled from P$_2$O$_5$ under N$_2$ [(n—Bu)$_4$N]$_2$ [Pt(CN)$_4$] was prepared from K$_2$[Pt(CN)$_4$].3H$_2$O (Aldrich) and [(n—Bu)$_4$N]Br (Aldrich) using literature methods (Mason, W. R., Gray, H. B. *J. Am. Chem. Soc.*, 1968, 90, 5721). All other reagents were used as received.

The synthesis of [Pt(p-CN—C$_6$H$_4$—CH$_3$)$_4$][Pt(CN)$_4$] is given as an example. A solution containing 0.270 g (2.30 mmol) p-CN—C$_6$H$_4$—CH$_3$ and 0. 152 g (0.436 mmol) cis-(CH$_3$CN)$_2$ PtCl$_2$ in 20 mL of CH$_3$CN was stirred under argon for 20 minutes. To this, 0.753 g (0.960 mmol) of solid [(n—Bu)$_4$N]$_2$[Pt(CN)$_4$] was added with vigorous stirring, resulting in the immediate formation of a blue precipitate.

After stirring the solution for 1 hour, the solid was collected on a medium frit and washed with three 10 mL portions of cold acetonitrile. The blue solid was dried overnight in vacuo to yield 0.339 g of product.

[Pt(p-CN—$C_6H_4$—$CH_3$)$_4$][Pt(CN)$_4$]. Yield=81%. mp 185°–189° C. (dec). IR (film) (cm$^{-1}$): ν(R—NC)=2258 s, 2215 w, ν(CN)=2126 m. VIS-NIR (film): $\lambda_{max}$=744 nm. Anal. Calcd for $C_{36}H_{28}N_8Pt_2$: C, 44.91; H, 2.93; N, 11.64. Found: C, 44.20; H, 2.72; N, 11.40.

(Pt(p-CN—$C_6H_4$—$C_6H_{13}$)$_4$][Pt(CN)$_4$]. Yield=65%. mp 155°–158° C. (dec). IR (film) (cm$^{-1}$): ν(R—NC)=2258 s, 2217 w, ν(CN)=2126 m. VIS-NIR (film): $\lambda_{max}$=841 nm. Anal. Calcd for $C_{56}H_{68}N_8Pt_2$: C, 54.10; H, 5.5 1; N, 9.01. Found: C, 54.07; H, 5.31; N, 9.03.

[Pt(p-CN—$C_6H_4$—$C_{10}H_{21}$)$_4$][Pt(CN)$_4$]. Yield=56%. mp 143°–147° C. (dec). IR(film) (cm$^{-1}$): ν(R—NC)=2256 s, 2219 w, ν(CN)=2126 m. VIS-NIR (filter paper): $\lambda_{max}$=746 nm. Anal. Calcd for $C_{72}H_{100}N_8Pt_2$: C, 58.92; H, 6.87; N, 7.63. Found: C, 59.16; H, 6.74, N, 7.33.

[Pt(p-CN—$C_6H_4$—$C_{12}H_{25}$)$_4$][Pt(CN)$_4$]. Yield=53%. mp 130°–134° (dec). IR(film) (cm$^{-1}$): ν(R—NC)=2255 s, 2217 w, ν(CN)=2125 m. VIS-NIR (filter paper): $\lambda_{max}$=764 nm. Anal. Calcd for $C_{80}H_{116}N_8Pt_2$: C, 60.8 1; H, 7.40; N, 7.09. Found: C, 60.99; H, 7.39; N, 7.04.

[Pt(p-CN—$C_6H_4$—$C14H_{29}$)$_4$][Pt(CN)$_4$]. Yield=20%. mp 108°–110° C. (dec). IR(film) (cm$^{-1}$): ν(R—NC)=2256 s, 2212 w, ν(CN)=2125 m. VIS-NIR (filter paper): $\lambda_{max}$=690 nm. Anal. Calcd for $C_{88}H_{132}N_8Pt_2$: C, 62.46, H, 7.86; N, 6.62. Found: C, 63.94; H, 8.23, N, 6.14.

[Pt(p-CN—$C_6H_4$—$C_{10}H_{21}$)$_4$][Pt(NO$_2$)$_4$]. A solution containing 0.426 g (1.74 mmol) p-decylphenylisonitrile, 0.1545 g (0.4439 mmol) cis-(CH$_3$CN)$_2$PtCl$_2$ (Aldrich), and 0.380 g (0.440 mmol) [(n-C$_4$H$_9$)$_4$N]2[Pd(CN)$_4$] in 8 mL of acetonitrile was stirred under argon for 90 minutes. During this time, a yellow-orange precipitate slowly formed. The solid was collected on a medium frit and washed with three 2-mL portions of acetonitrile. As the solid dried on the frit, the color changed from yellow to orange. Upon contact with acetonitrile, the solid immediately turned yellow. Recrystallization from benzene/acetone and drying overnight in vacuo afforded 0.495 g of product (72%). IR (film): ν(R—N≡C) =2264 s, 2198 w cm$^{-1}$, ν(NO)=1402 s, 1380 vs, 1334 s cm$^{-1}$. UV-VIS (film): $\lambda_{max}$=493 nm. Emission (film, $\lambda_{ex}$= 493 nm): $\lambda_{max}$=605 nm. Anal. Calcd for $C_{68}H_{100}N_8O_8Pt_2$: C, 52.77; H, 6.51; N, 7.24. Found: C, 52.64; H, 6.47; N, 7.20.

Instrumental Techniques.

Vis-NIR absorption spectra were recorded with a Tracor Northern TN-6500 rapid scan diode-array spectrometer with a tungsten lamp light source (Bullock, J. P.; Mann, K. R., Inorg. Chem., 1989, 28, 4006) or with a Nicolet Magna 5.50 NIR spectrometer. Emission spectra in the NIR region (700–1300 nm) were recorded with a SPEXI 12X spectrofluorometer equipped with an InGaAs photodiode operated in intensity mode. The signal was modulated using a Stanford Research Systems SR510 Lock-In amplifier and SR540 Optical Chopper. An Oriel #57385 short bandpass filter was positioned in the excitation beam to derease noise. Spectra were corrected for monochrometer and detector responsive, after a background spectrum of clean filter paper had been subtracted. Sample films of the double-complex salts were coated on 3.0×0.5 cm filter paper strips from hexane suspensions as previously described. A coated strip was held against the inside wall of a 4-sided quartz cell by a copper spring. A beaker was placed inside the cell to contain the solvents. After solvent was added to the beaker, the cell was covered, and at least 5 minutes were allowed for the equilibrium vapor pressure to be established before spectra were taken.

Infrared absorption spectra were obtained by an attenuated total reflectance (ATR) method using a Nicolet Magna-IR System 550 spectrometer, equipped with a ZnSe trough HATR (Horizontal Attenuated Total Reflectance) cell from PIKE Technologies. Data were processed using OMNIC 1.2 software. Sample films were coated on the ZnSe crystal from either a CHCl$_3$ solution or hexane suspension. Films of the double-complex salts were washed with acetone prior to taking spectra to remove impurities and decomposition products. A beaker was placed on the ZnSe crystal mount to contain the solvents. After solvent was added to the beaker, the film and crystal mount were covered, and numerous spectra were recorded before and after equilibrium vapor pressure was established.

The double complex salts were prepared by the modification of a previously described method (Exstrom, et al. supra; and Nagel, supra). Addition of the appropriate isonitrile to a solution of cis-(CH$_3$CN)$_2$PtCl$_2$ in acetonitrile was followed by addition of [(n-Bu)$_4$N]$_2$|Pt(CN)$_4$]. The complexes were isolated as blue, insoluble solids in yields that ranged from 20 to 81%. The compounds are stable indefinitely in the solid state, but as reported by Keller and Lorenz (Keller, H. J., Lorenz, R., Z. Naturforsch. B., 1976, 31B, 565–568) for similar compounds, we observed a slow decomposition reaction for solutions of the [Pt (arylisonitrile)$_4$][Pt(CN)$_4$] complexes in chlorinated solvents. The decomposition rate decreases in the order CH$_2$Cl$_2$>CHCl$_3$>>CCl$_4$ This decomposition reaction is much slower ($t_{1/2}$ is on the order of 8 days for CH$_2$Cl$_2$) than the corresponding reaction observed for the [Pt (arylisonitrile)$_4$][Pd(CN)$_4$]analogs ($t_{1/2}$'s on the order of hours).

All of the compounds studied in the solid state exhibit a prominent electronic transition at the edge of the visible, extending well into the near infrared spectral region. We assign the absorption to a spin allowed component of the d-sigma* to p-sigma transition that arises from a linear stack of alternating cations and anions. Vis-NIR absorption spectra of the homometallic double complex salts ([Pt (arylisonitrile)$_4$][Pt(CN)$_4$]) of solid-state dispersions on filter paper show that the position of the low energy band varies somewhat unpredictably with the alkyl substituent chain length. We believe that this variation is due to changes in the stacking interactions between the cations and anions caused by crystal packing effects rather than differences in the electronic effect of the substituent on the cation energy levels. In comparison to the Pt Pd analog compounds, the low energy band is shifted approximately 5000 cm$^{-1}$ lower in energy. This large shift is indicative of an increase in the M—M interaction between the cation and anion in the homometallic compounds (Smith, T. P. Ph.D. Dissertation, California Institute of Technology, 1982). Additionally, the compounds exhibit an intense emission band in the NIR (Table 1). These emission bands are (tentatively) assigned to spin allowed component of the p-sigma to d-sigma* transition; a more definitive assignment must await emission lifetime measurements. In any event, these compounds are a very select group of transition metal complexes that emit in the NIR spectral region ((a) Savoie, C.; Reber, C., Belonger, S., Beauchamp, A. L. Inorg. Chem., 1995, 34, 385 1: (b) Juris, A.; Balzani, V.; Campagna, S.; Denti, G.; Serroni, S.; Frel, G.; Gudel, H. U. Inorg. Chem., 1994, 33, 1491; (c) Vincze, L.; Friesen, D. A.; Mezyk, S. P.; Waltz, W. L. Inorg. Chem., 1992, 31, 4950; (d) Bilsel, O.; Rodriguez, J.; Milam, S. N.; Gorlin, P. A.; Girolami, G. S.; Suslick, K. S.; Holten, D. J. *Am. Chem. Soc.*, 1992, 114, 6528; (e) Stranger, R.; Moran, G.; Krausz, E.; Dubicki, L.; Gudel, H. Furer, N. *Inorg. Chem.*, 1992, 31, 2860; (f) Mosseri, S.; Mialocq, J. C.; Perly, B. Hambright, P. *J. Phys. Chem.* 1991, 95, 2196; (g) Davis, M.; Reber, C. *J. Luminesc.*, 1994, 60, 1. (h) Richter, M. M.; Brewer, K. J. *Inorg. Chem.*, 1993, 32, 5762; (I) Matsul, K.; Nazeeruddin, M. K.; Humphrybaker, R.; Gratzel, M.; Kalyanasundaram, K. *J. Phys. Chem.* 1992, 96, 10587; U) Herren, M.; Gudel, H. U. *Inorg. Chem.*, 1992, 31, 3683; (k) Reber, C., Gudel, H. U. *J. Luminesc.*, 1988,42, 1; (1) Yao, Q.; Maverick, A. W. *Inorg Chem.*, 1988, 27, 1669.

The stacked nature of the [Pt(arylisonitrile)$_4$][Pt(CN)$_4$] solids is further supported by the dramatic temperature dependence of the NIR absorption band. For example, upon cooling a "dry" film of [Pt(p-CN—C$_6$H$_4$—C$_{10}$H$_{21}$)$_4$][Pt(CN)$_4$] from room temperature to 77K, the absorption band maximum shifts from 746 to 846 nm, and the emission band maximum shifts from 944 to 1094 nm. This diagnostic red shift is observed in the solid state spectra of stacked complexes because the thermal lattice contraction caused by cooling results in shorter metal-metal distances (Gliemann, supra; and Palmans, R.; Frank, A. J.; Houlding, V. H.; Miskowski, V. M. *J. Mol. Catal.* 1993, 80, 327).

Qualitatively, the response of |Pt(arylisonitrile)$_4$][Pt(CN)$_4$] to VOCs as a function of chain length is similar to the [Pt(arylisonitrile)$_4$]|Pd(CN)$_4$] compounds previously studied, with an ordering of 10>>6>1, 12>14. The time scale of VOC sorption is also similar for the two sets of compounds (t$_{1/2}$<50 ms). In general, the NIR shifts exhibited by [Pt(p-CN—C$_6$H$_4$—C$_{10}$H$_{21}$)$_4$][Pt(CN)$_4$] are 2–3 times greater than those observed for the Pd(CN)$_4^{2-}$ salt (see Table 1). Among the solvents we have tested, ethanol, 2-propanol, acetonitrile, and acetone affect the peak position of the Pt(CN)$_4^{2-}$ substantially more than they do the Pd(CN)$_4^{2-}$ salt, but the general order of solvent effects is the same for both M(CN)$_4^{2-}$ salts. The increase in the shift observed for the Pt(CN)$_4^{2-}$ salts suggests that the solvent interacts with the chromophore relatively more strongly in the Pt(CN)$_4^{2-}$ salt than in the Pd(CN)$_4^{2-}$ salt.

Figure 2:
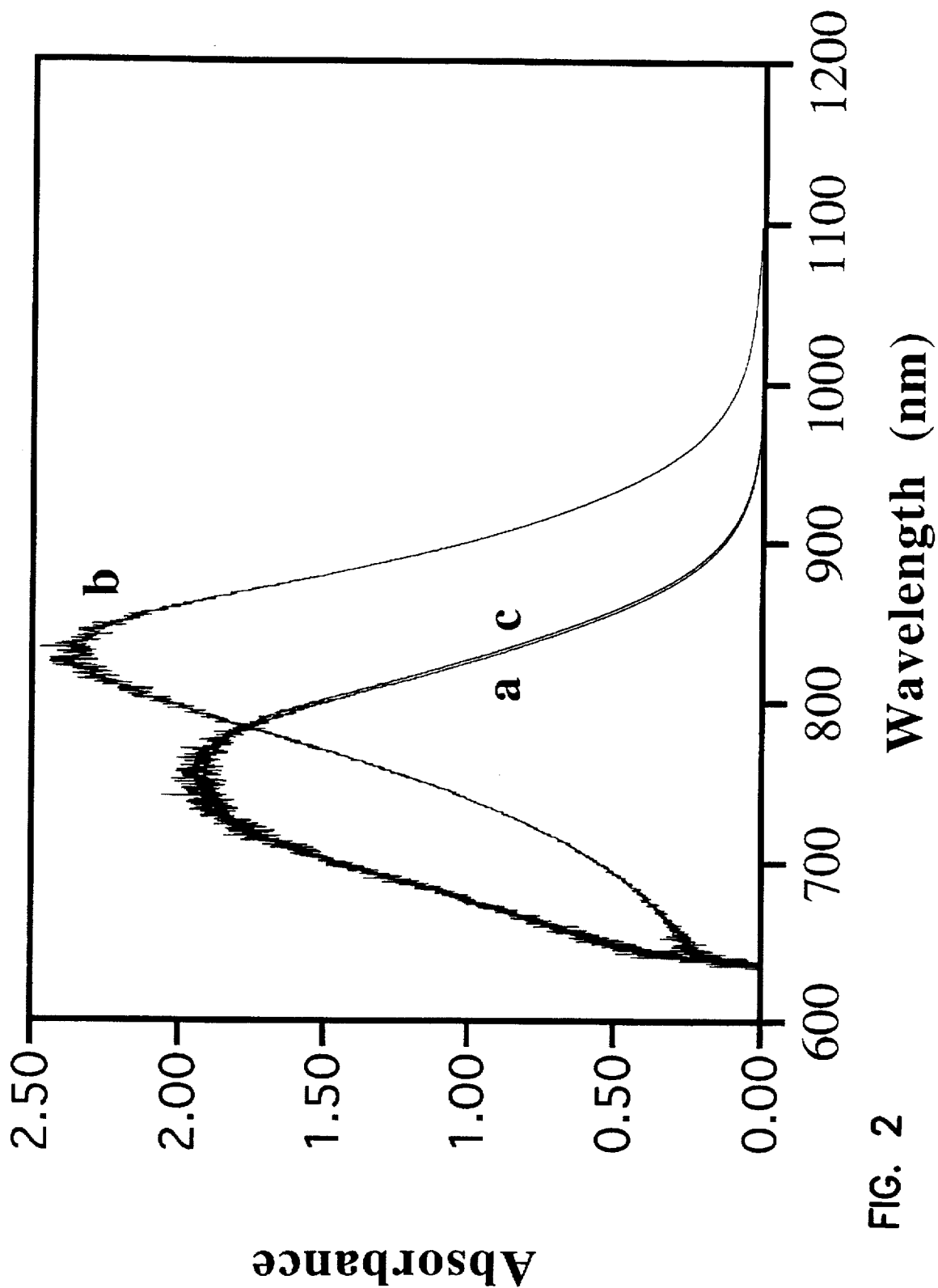
FIG. 2 is a graph of Vapochromic Response of a thin film of [Pt(CN—$C_6H_4$—$C_{10}H_{21}$)$_4$][Pt(CN)$_4$] on a ATR crystal. (a) "Dry" film, (b) Film in the presence of dichloromethane vapor; (c) Removal of dichloromethane shifts the spectrum back to the "dry" state. Curves (a) and (c) are virtually superimposable.
Figure 3:
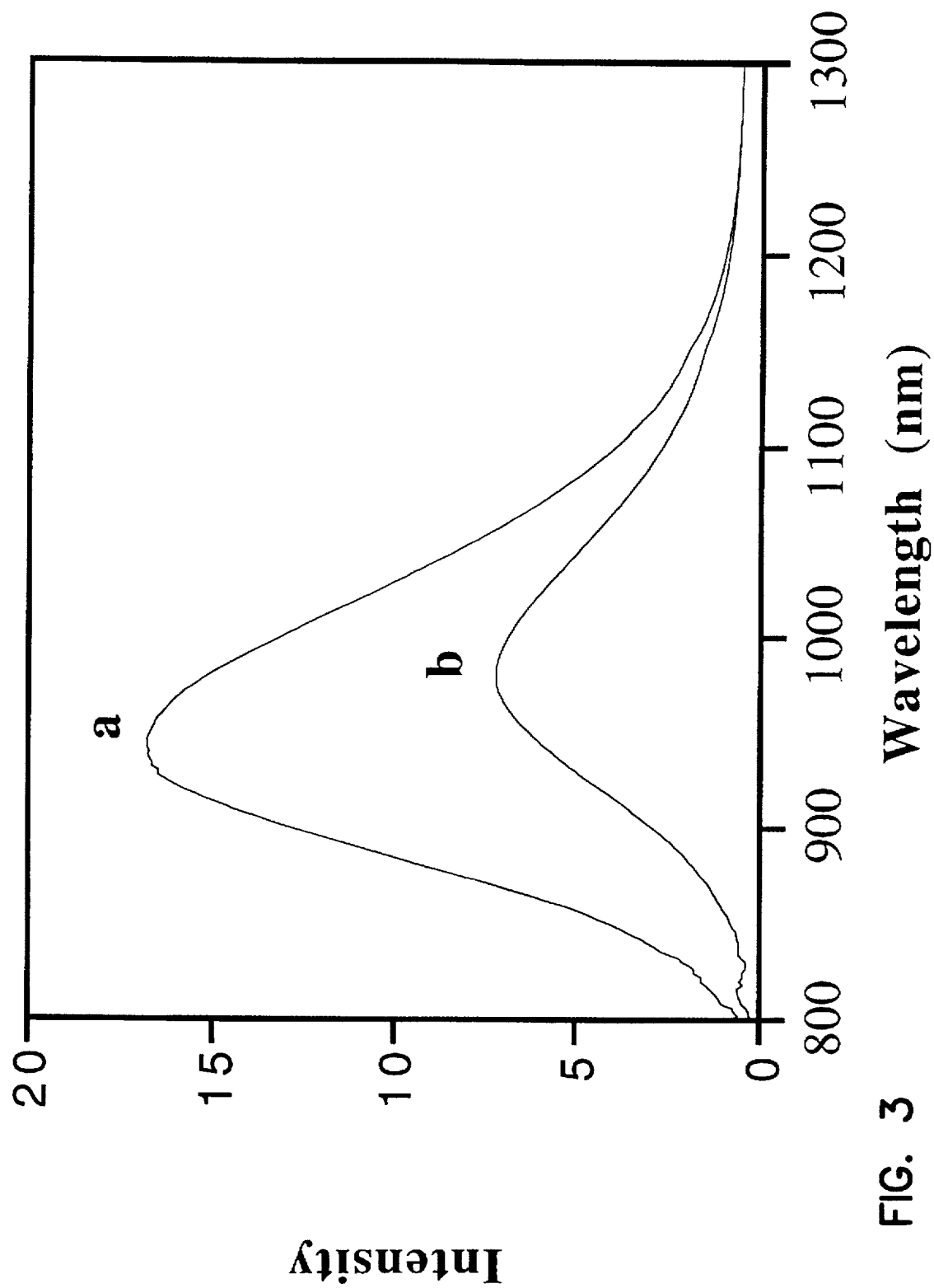
FIG. 3 is a graph of room temperature emission spectra of a [Pt(CN—$C_6H_4$—$C_{10}H_{21}$)$_4$][Pt(CN)$_4$] dispersion on filter paper excited at lambda max=725 nm. Curve (a) represents a "dry" sample; curve (b), the same sample in the presence of air saturated with $CH_2Cl_2$ vapor.

We have studied in greatest detail the vapochromic shifts in the low energy NIR absorption and emission bands of solid-state films of [Pt(p-CN—C$_6$H$_4$—C$_{10}$H$_{21}$)$_4$][Pt(CN)$_4$] (the n=10 compound). This compound is responsive and shows high sensitivity and stability in its vapochromic response to a wide range of VOC compounds. As summarized in Table 2, the absorption bands of the solid-state films of [Pt(p-CN—C$_6$H$_4$—C$_{10}$H$_{21}$)$_4$][Pt(CN)$_4$] shift from 11 to 91 nm (190–1500 cm$^{-1}$) lower in energy upon exposure to VOCs. The particularly large change in the Vis-NIR absorption spectrum that occurs when dichloromethane contacts a film of [Pt(p-CN—C$_6$H$_4$—C$_{10}$H$_{21}$)$_4$][Pt(CN)$_4$] on an ATR crystal is shown in FIG. 2. The peak shifts nearly isosbestically from 746nm to 811 nm as the VOC equilibrates with the solid. Repeated cycles of dichloromethane exposure and removal causes no changes in the spectral sequences observed. A similar shift occurs in the emission bands of the solid-state films of [Pt(p-CN—C$_6$H$_4$—C$_{10}$H$_{21}$)$_4$][Pt(CN)$_4$] (FIG. 3, Table 1) but the shifts in the emission band are somewhat smaller than those observed for the absorption band and range between 2 to 72 nm (22–770 cm$^{-1}$) lower in energy upon exposure to VOCs.

IR spectroscopy studies were useful for characterizing interactions between the cations and anions in the solid compounds. The solid-state infrared spectrum of a dry [Pt—CN—C$_6$H$_4$—C$_{10}$H$_{21}$)$_4$][Pt(CN)$_4$] film shows single bands at 2259 (v(CNR)) and 2125 cm$^{-1}$ (v(CN)). The v(CN) isonitrile stretching frequency in the |Pt(CN—C$_6$H$_4$—C$_{10}$H$_{21}$)$_4$]|Pt(CN)$_4$] compound is substantially shifted from the free ligand value (2130 cm$^{-1}$). This shift to higher energy is consistent with strong sigma donation of the CN—C$_6$H$_4$—C$_{10}$H$_{21}$ isonitrile ligand to the Pt(II) and is in agreement with v(CN) isonitrile stretching frequencies previously reported for other Pt(CN)$_4^{2-}$ complexes with noninteracting counterions. The modest shift in the v(CN) cyanide stretching frequency for [Pt(CN—C$_6$H$_4$—C$_{10}$H$_{21}$)$_4$][Pt(CN)$_4$] (2125 cm$^{-1}$) relative v(CN) observed (2118 cm$^{-1}$) for the [t-Bu$_4$N$_{-2}$]$_2$[Pt(CN)$_4$] precursor suggests that there is little ground state charge transfer between anion and cation imposed by the Pt—Pt stacking of the double complex salt structure.

Figure 4:
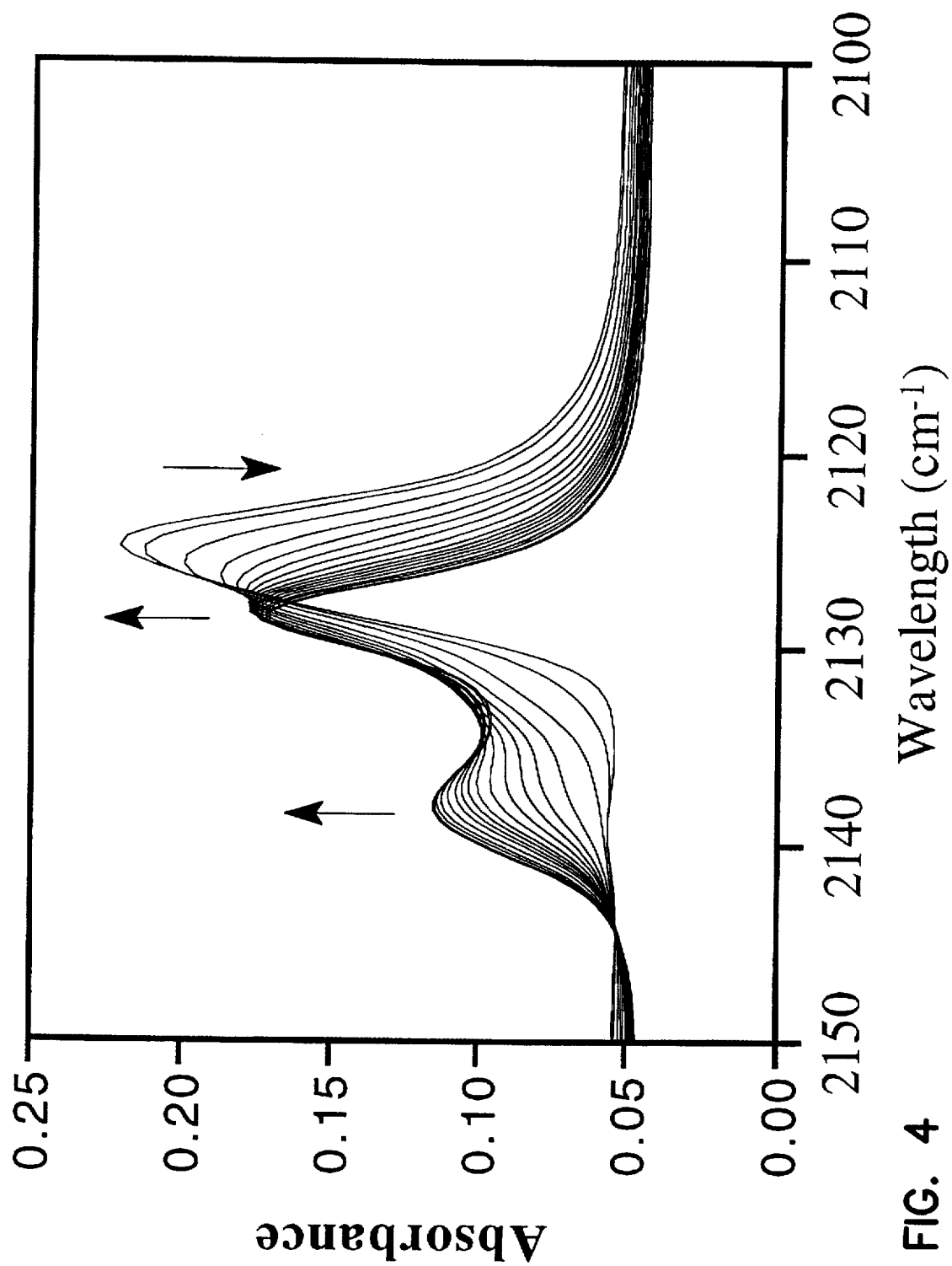
FIG. 4 is a graph of an ATR-FTIR spectral study of [Pt(CN—$C_6H_4$—$C_{10}H_{21}$)$_4$][Pt(CN)$_4$] as the air inside the sample compartment is saturated with methanol vapor. Arrows indicate the direction of change. Spectra were taken at ca. 20 s. intervals.

IR spectroscopy was also useful for gaining insight into the nature of the interactions between the VOC and the components of the solid that lead to the vapochromic shifts. Infrared bands attributable to the adsorbed organic molecule are observed in infrared spectra of films of the [Pt(CN—C$_6$H$_4$—C$_{10}$H$_{21}$)$_4$]|Pt(CN)$_4$] complex. We have observed that when a solid film on the surface of the ATR crystal dissolves, a large increased in absorbance occurs. This has been previously attributed to better contact between the solution film and the crystal surface. (See: Ingle, J. D., Jr.; Crouch, S. R. *Spectrochemical Analysis*, Prentice Hall: Englewood Cliffs, N.J., 1988, pp. 429–434). These interactions could be due to a complicated mix of lypophilic, dipole—dipole and/or hydrogen bonding interactions. Exposure of [Pt(CN—C$_6$H$_4$—C$_{10}$H$_{21}$)$_4$]|Pt(CN)$_4$] film to any of the VOC vapors in Table 2 results in no shift in the v(CNR) isonitrile stretching frequency, but the v(CN) cyanide stretch exhibits a reversible shift to higher frequency of 0–15 cm$^{-1}$ (see Table 2, FIG. 4). [The magnitude of these shifts is on the order of the 7 cm$^{-1}$ shift that occurs when the solid state structure is formed from the ionic precursors.] As in the case of the Vis-NIR absorption band, removal of the VOC vapor source causes the IR spectrum to revert to that of the dry film for all the VOCs studied. The largest shifts in the v(CN) cyanide stretch are produced by the VOCs capable of hydrogen bonding, while aprotic VOCs cause little or no v(CN) shifts. In addition to the shift, exposure of |Pt(CN—C$_6$H$_4$—C$_{10}$H$_{21}$)$_4$][Pt(CN)$_4$] to CHCl$_3$ or alcohol vapor causes the v(CN) cyanide band to split into two bands spaced 5–10 cm$^{-1}$ apart. The two v(CN) bands in the VOC-saturated [Pt(CN—C$_6$H$_4$—C$_{10}$H$_{21}$)$_4$][Pt(CN)$_4$] IR spectrum indicate that at least two different cyanide environments per [Pt(CN)$_4$]$^{2-}$ unit are present in the solid. The combined integrated area under these bands is nearly equal to that for the single v(CN) band of the dry film, indicating that the double complex salt remains in the solid phase upon sorption of the VOC (Kieman, P. M., Ludi, A. *J. Chem. Soc. Dalton. Trans.* 1978, 1127). This observation is also consistent with our previously reported X-ray powder diffraction studies of [Pt(CN—C$_6$H$_4$—C$_{10}$H$_{21}$)$_4$][Pt(CN)$_4$], which showed that the crystallinity of the double complex salt is not significantly affected by the sorption of VOCs (Exstrom, vide supra).

The shifts that we report for the cyanide v(CN) stretch are analogous (but somewhat smaller) than the irreversible shifts reported for solid K$_2$Ni(CN)$_4$ ((a) James, D. W.; Nolan, M. J. *Aust. J. Chem.* 1973, 26, 1433–1441. (b) Nakamoto, K.; Fujita, J.; Murata, H. *J. Am. Chem. Soc.* 1958, 80, 4817–4823) and Fe(phen)$_2$(CN)$_2$ (phen=1,10-phenanthroline) (Atoji, M.; Richardson, J. W.; Rundle, R. E. *J. Am. Chem. Soc.* 1957, 79, 3017) when they are exposed to the powerful Lewis acid BF$_3$. As in the case of the BF$_3$ results, we suggest that the v(CN) shift results from interactions involving the cyanide lone pair on N and the VOC guest molecule. Although this simple interaction model suggests that a direct correlation between the ν(CN) shift and VOC Lewis acidity (or hydrogen-donating ability) should be observed, two particularly intriguing results with benzene and water suggest that the vapochromic shifts in the IR (and the Vis-NIR) may not correlate perfectly and may arise from more complicated interactions within the solid or at the solid/gas interface. Benzene exhibits a relatively large vapochromic shift in the NIR but a small ν(CN) cyanide shift, while water echils no vapochromic response from any of the compounds studied here. The benzene results suggest that lypophilic interactions with the isonitrile ligands that do not result in substantial ν(CN) shifts may also be important in producing vapochromic shifts. (Solid state $^{13}C$ NMR studies are planned to address this issue.) In the case of the results with the strong hydrogen-bonder, water, the lack of a Vis-NIR vapochromic response or a ν(CN) shift strongly suggests that water is unable to penetrate the solid. The network produced by stacking the long n-decyl chains of the isonitrile ligands in the structure may produce a hydrophobic barrier at the solid/gas interface through which water is unable to pass. (Further studies will be needed to address this (presumably) kinetic effect.)

We have synthesized the homometallic [Pt(arylisonitrile)$_4$][Pt(CN)$_4$] analogs for comparison with the previously reported mixed metal [Pt(arylisonitrile)$_4$][Pd(CN)$_4$] compounds. Vis-NIR and IR studies allow several conclusions to be drawn:

1. [Pt(arylisonitrile)$_4$][Pt(CN)$_4$] compounds exhibit strong absorptions and emission bands in the NIR spectral region due to excitations of an electronic transition that is characteristic of M—M chains of dg metal ions. The NIR emission properties are particularly noteworthy.

2. Solutions in and solid films in contact with chlorinated solvents of the Pt—Pt compounds are more stable than the Pt Pd analogs.

3. The absorption and emission bands of the Pt—Pt compounds are substantially red shifted from those observed in the Pt-Pd compounds.

4. The position of $\lambda_{max}$ abs in the dry films and the magnitude of the vapochromic effect in the Vis-NIR are a function of the alkyl substituent chain length.

5. IR spectra of solid films suggest that VOCs capable of H-bonding interact strongly with the Pt(CN)$_4^{2-}$ group in the solid.

6. Exposure to non-polar VOCs (i.e., benzene) does not cause large shifts in the ν(CN) IR spectral region but never the less results in substantial vapochromic effects in the NIR. The vapochromism in this case must be attributed to lypophilic interactions.

7. The compounds are unresponsive to water vapor in the NIR and in the IR spectral regions.This may be due to important hydrophobic interactions at the solid/gas interface.

Synthesis and General Properties of [Pt(p-CN—C$_6$H$_4$—C$_{10}$H$_{21}$)$_4$][Pt(NO$_2$)$_4$].

Reacting [(n-C$_4$H$_9$)$_4$N]$_2$[Pt(NO$_2$)$_4$] with (CH$_3$CN)$_2$PtCl$_2$ and p-CN—C$_6$H$_4$—C$_{10}$H$_{21}$ results in a bright orange solid characterized by IR and elemental analysis to be [Pt(p-CN—C$_6$H$_4$—C$_{10}$H$_{21}$)$_4$][Pt(NO$_2$)$_4$]. Unlike its [M(CN)$_4$]$^{2-}$ (M=Pd, Pt) counterparts, [Pt(p-CN—C$_6$H$_4$—C$_{10}$H$_{21}$)$_4$][Pt(NO$_2$)$_4$] is soluble and stable in benzene, tetrahydrofuran (THF), and halogenated solvents for 1–2 days. [Pt(p-CN—C$_6$H$_4$—C$_{10}$H$_{21}$)$_4$][Pt(NO$_2$)$_4$] has a sticky, amorphous texture, even after recrystallization from benzene/acetone. The bright orange color is due to an intense visible absorption band ($\lambda_{max}$=493 nm) due to the dσ*→p$_z$,π* (NO$_2$) transition created by Pt—Pt stacking interactions. This band is markedly blue shifted compared to that of C10-PtPt (i.e., decyl substituted isonitrile, (p-CN—C$_6$H$_4$—C$_{10}$H$_{21}$). The electron-withdrawing nature of the NO$_2^-$ ligands, along with the possibility of greater Pt—Pt separations, would be expected to decrease Pt—Pt interactions, increasing the dσ*→p$_z$,π*(NO$_2$) transition energy.

Figure 5A:
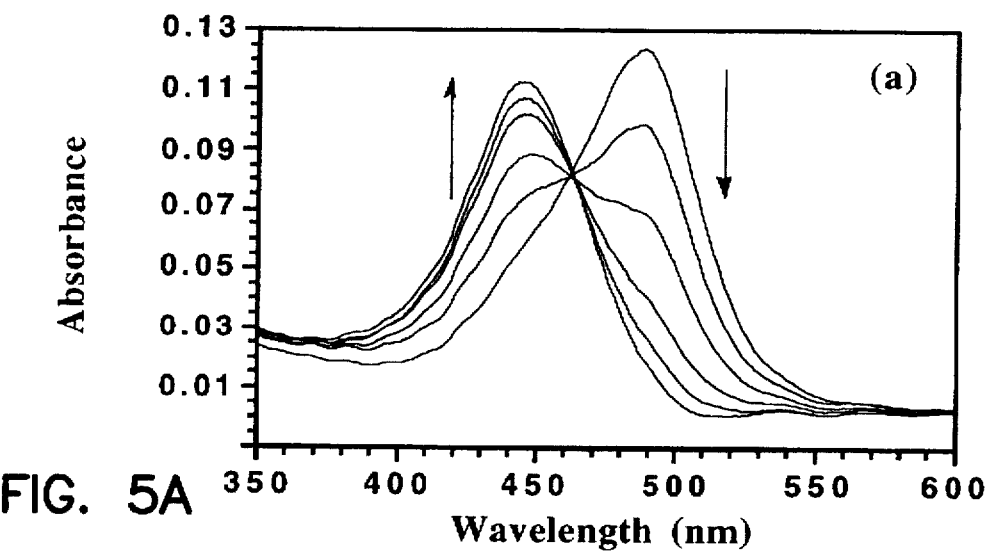
FIG. 5 is a graph of Solid-state absorption spectra of. (a) a [Pt(p-CN—$C_6H_4$—$C_{10}H_{21}$)$_4$][Pt(NO$_2$)$_4$] (orange form) film dispersed on a microscope slide upon exposure to benzene vapor. (b) a [Pt(p-CN—$C_6H_4$—$C_{10}H_{21}$)$_4$][Pt(NO$_2$)$_4$] (yellow form) film dispersed on a microscope slide upon exposure to acetone vapor.
Figure 5B:
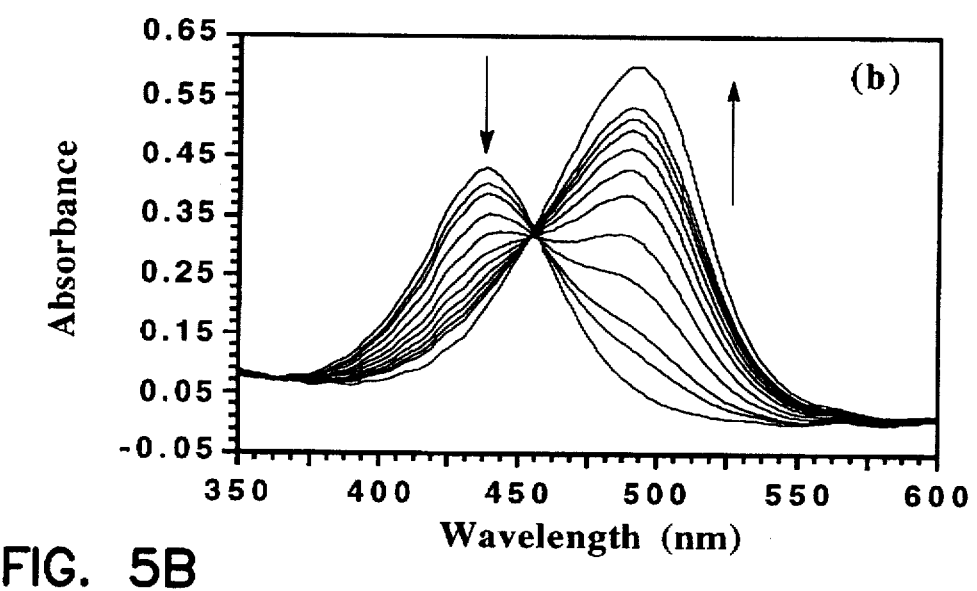

Exposure of a [Pt(p-CN—C$_6$H$_4$—C$_{10}$H$_{21}$)$_4$][Pt(NO$_2$)$_4$] film to benzene, THF, or chlorinated solvent vapor results in an isosbestic shift in the visible absorption maximum from 493 to 441 nm. By eye, the film color changes from orange to yellow. In FIG. 5a are a sequence of solid state transmission UV-vis absorption spectra showing the time response of a [Pt(p-CN—C$_6$H$_4$—C$_{10}$H$_{21}$)$_4$][Pt(NO$_2$)$_4$] film when exposed to room temperature air saturated with benzene vapor. Upon removal of the vapor, the film color does not return to orange. However, exposing this yellow form to solvent vapor in which [Pt(p-CN—C$_6$H$_4$—C$_{10}$H$_{21}$)$_4$]∥Pt(NO$_2$)$_4$] does not dissolve causes the absorption maximum shift isosbestically back to 493 nm and the film color changes from yellow back to orange. FIG. 5b shows a series of UV-vis absorption spectra of a film of [Pt(p-CN—C$_6$H$_4$—C$_{10}$H$_{21}$)$_4$][Pt(NO$_2$)$_4$] (yellow form) upon exposure to acetone vapor. The vapochromic responses are irreversible, but the original "dry" spectrum can be regenerated. This property of the [Pt(p-CN—C$_6$H$_4$—C$_{10}$H$_{21}$)$_4$]∥Pt(NO$_2$)$_4$] material, along with the selectivity toward only benzene, THF, and halogenated solvent vapor, allows for the use of this material as a VOC sensor in areas that are not under constant surveillance (i.e., so one can determine if that area was exposed to VOCs at some point in the past).

As expected, the IR spectrum of [Pt(p-CN—C$_6$H$_4$—C$_{10}$H$_{21}$)$_4$]∥Pt(NO$_2$)$_4$] exhibits a single ν(R—CN) band (with a weak, low-energy shoulder) consistent with a D$_{4h}$ symmetry of the [Pt(CNR)$_4$]$^{2+}$ unit. However, there are three ν(NO) bands (asymmetric NO stretches: 1402 and 1380 cm$^{-1}$; symmetric NO stretch: 1334 cm$^1$), indicating that the ligands in the [Pt(NO$_2$)$_4$]$^{2-}$ units are not all coplanar.

Synthesis of Neutral Complexes.

The syntheses of Pt(p-CN—C$_6$H$_4$—C$_{10}$H$_{21}$)(p-C═NH(OEt)—C$_6$H$_4$—C$_{10}$H$_{21}$)(CN)$_2$, Pt(p-CN—C$_6$H$_4$—CH$_3$)$_2$(CN)$_2$ and Pt(p-CN—C$_6$H$_4$—C$_{10}$H$_{21}$)$_2$(CN)$_2$ are given as typical examples of neutral complexes, the analogs differing only with alkyl chain length of the isonitrile or the alcohol used in the synthesis. Neutral Pt(II) stacking complexes containing CN$^-$ and isonitriles were prepared either by reacting 2 equivalents of RNC with Pt(CN)$_2$ or refluxing the appropriate [Pt(CNR)$_4$][Pt(CN)$_4$] complex double-salt in CHCl$_3$. All reactions were performed under an argon atmosphere. Acetonitrile was distilled from P$_2$O$_5$ under N$_2$ and run through an activated alumina (neutral washed) column immediately prior to use. Other solvents were used as received. Pt(CN)$_2$ (Strem Chemical Company) was also used as received.

Pt(p-CN—C$_6$H$_4$—C$_{10}$H$_{21}$)(p-C═NH(OEt)—C$_6$H$_4$—C$_{10}$H$_{21}$)(CN)$_2$. A solution of 1.00 g (0.170 mmol) [Pt(CN—C$_6$H$_4$—C$_{10}$H$_{21}$)$_4$]∥Pt(CN)$_4$] was refluxed in 125 mL CHCl$_3$ (stabilized with 0.75% EtOH) for 72 hr., during which the solution turned from deep blue to colorless. The solvent was removed by rotary evaporation, leaving a bright yellow-orange solid. This crude product was purified by column chromatography using silica and 85:15 CH$_2$Cl$_2$:ethyl acetate as the stationary and mobile phases, respectively. The major fraction was isolated and the solvent removed by rotary evaporation, leaving a bright orange solid. Drying in vacuo overnight afforded 0.640 g (64% yield) orange powder. FABMS 780 (M)$^+$, 734 (M-EtOH)$^+$; IR (film): $\nu$(N—H)= 3380 w cm$^{-1}$, $\nu$(RC≡N)=2242 s, 2222 vs cm$^{-1}$, $\nu$(C≡N) =2162 s, 2156 sh cm$^{-1}$, $\nu$(C=N)=1542 m cm$^{-1}$; UV-VIS (film): $\lambda_{max}$=490 nm; Emission (film, $\lambda_{ex}$=490 nm): $\lambda_{max}$= 600 nm.

Pt(p-CN—$C_6H_4$—$CH_3$)$_2$(CN)$_2$. A solution of 0.500 g (2.02 mmol) Pt(CN)$_2$ and 0.510 g (4.35 mmol) p-CH$_3$—$C_6H_4$—NC was stirred in 40 mL CH$_3$CN for 48 hr., during which a bright red precipitate formed. This was filtered, recrystallized from CH$_2$Cl$_2$/hexanes, and dried in vacuo to afford 0.541 g (56%) of red powder. $^1$H NMR (CD$_2$Cl$_2$) $\delta$ 7.22 (q, 4 H, Ph), 2.36 (s, 3 H, CH$_3$); IR (film): $\nu$(RC≡N) =2242 s, 2222 vs cm$^{-1}$, $\nu$(C≡N)=2162 s, 2156 sh cm$^{-1}$, UV-VIS (film): $\lambda_{max}$=522 nm. Anal. Calcd for C$_{20}$H$_{14}$N$_4$Pt: C, 44.91; H, 2.93; N, 11.64. Found: C, 45.06; H, 3.00; N, 11.44.

Pt(p-CN—$C_6H_4$—$C_{10}H_{21}$)$_2$(CN)$_2$. A solution of 0.301 g (1.22 mmol) Pt(CN)$_2$ and 0.600 g (2.47 mmol)p-$C_{10}H_{21}$—$C_6H_4$—NC was stirred in 15 mL CH$_3$CN for 72 hr., during which the solution turned orange-red and cloudy. The solvent was removed by rotary evaporation, and the remaining solid was redissolved in 25 mL CH$_2$Cl$_2$ and filtered through a small celite column. The filtrate solvent was removed by rotary evaporation, leaving a bright red-orange solid. This crude product was purified by column chromatography using silica and 85:15 CH$_2$Cl$_2$:ethyl acetate as the stationary and mobile phases, respectively. The major fraction was isolated and the solvent removed by rotary evaporation, leaving a bright red solid. Drying in vacuo overnight afforded 0.516 g (58% yield) red powder. $^1$H NMR (CD$_2$Cl$_2$) $\delta$ 7.60 (d, 2 H, Ph), 7.30 (d, 2 H, Ph), 2.61 (t, 2 H, (CH$_2$)Ph), 1.22 (m, 16 H, CH$_2$), 0.78 (t, 3 H, CH$_3$); IR (film): $\nu$(RC≡N)=2240 s, 2222 vs cm$^{-1}$, $\nu$(C≡N)=2162 s, 2158 sh cm$^{-1}$, UV-VIS (film): $\lambda_{max}$=515 nm. Anal. Calcd for C$_{38}$H$_{50}$N$_4$Pt: C, 58.92; H, 6.87; N, 7.63. Found: C, 59.23; H, 6.94; N, 7.44.

Decomposition Studies of Pt(CN—$C_6H_4$—$C_{10}H_{21}$)$_4$]|Pt (CN)$_4$].

Like their Pt-Pd analogs, Pt(CN—$C_6H_4$—$C_{10}H_{21}$)$_4$]|Pt (CN)$_4$] is insoluble in common solvents, with the exceptions of chlorinated solvents, in which deep blue or purple solutions are formed. In these solutions, the materials undergo a slow decomposition reaction that can be monitored by IR spectroscopy. The double-salt $\nu$(RN≡C) and $\nu$(CN) bands at 2256 and 2125 cm$^{-1}$, respectively, decrease in intensity, while new bands at 2238 (sh), 2220, 2146, and 2161 cm$^{-1}$ grow in. The first two bands are assigned to $\nu$(RN≡C) stretches, while the last two are assigned to $\nu$(CN) stretches. The splitting of each stretch into two IR bands is consistent with the cis structure of the Pt(CNR)$_2$(CN)$_2$ product. Refluxing a CHCl$_3$ solution of [Pt(CNR)$_4$]|PtCl$_4$] has been reported to give 2 equivalents of cis-Pt(CNR)$_2$Cl$_2$. While dissolving Pt(CN—$C_6H_4$—$C_{10}H_{21}$)$_4$]|Pt(CN)$_4$] in CH$_2$Cl$_2$ (approx. 0.01M solution) results in complete decomposition within 3 hours, the Pt(CN—$C_6H_4$—$C_{10}H_{21}$)$_4$]|Pt(CN)$_4$] decomposition rate is much slower and varies with solvent. Decomposition of Pt(CN—$C_6H_4$—$C_{10}H_{21}$)$_4$]|Pt(CN)$_4$] in CH$_2$Cl$_2$, CHCl$_3$, and CCl$_4$ (approximately 0.01M solution), is complete in 2, 6, and 14 days, respectively. This trend is opposite that for the 2-electron oxidation of binuclear Ir(I) and Rh(I) complexes by halogenated solvents, (Hill, M. G.; Mann, K. R. *Inorg Chem.* 1991, 30, 1429) suggesting that the decomposition mechanism for C10-PtPt features ligand dissociation and rearrangement as opposed to oxidation of the Pt centers. The $\nu$(CN) and $\nu$(RN≡C) IR band positions confirm that the metal centers remain Pt(II).

In an effort to isolate and characterize the Pt(CN—$C_6H_4$—$C_{10}H_{21}$)$_4$]|Pt(CN)$_4$] decomposition product(s), a CHCl$_3$ solution of Pt(CN—$C_6H_4$—$C_{10}H_{21}$)$_4$]|Pt(CN)$_4$] was refluxed until the solution color changed from deep purple to pale yellow or colorless. Removal of the solvent left a bright orange solid that possessed an intense visible absorption band at 490 nm corresponding to the d$\sigma$a*→p$_z$.$\pi$*(CN) transition. Unlike the powdery double-salt complexes, this orange decomposition product (Pt(p-CN—$C_6H_4$—$C_{10}H_{21}$) (p-C=NH(OEt)—$C_6H_4$—$C_{10}H_{21}$)(CN)$_2$) was sticky and had an amorphous texture. Unexpectedly, this compound exhibited only one $\nu$(RN≡C) band (2230 cm$^{-1}$) with two $\nu$(CN) bands (2147 and 2140 cm$^{-1}$). Further analysis revealed additional IR bands at 3380 and 1542 cm$^{-1}$, corresponding to $\nu$(N—H) and $\nu$(C=N) stretches, respectively. This suggests that the orange product consists of a Pt(II) center with two cyanide ligands, one isocyanide, and one imine ligand. Reaction of isocyanide-containing metal complexes with CH$_3$OH is known to convert one RNC ligand to R—NH=C(OCH$_3$),(Bonati, F.; Minghetti, G. *J. Organomet. Chem.* 1970, 24, 251–256) where the alkene carbon coordinates to the metal center as a "Fischer Carbene" (Fischer, E. O.; Massböl, A. *Angew. Chem. Int. Ed. Engl.* 1964, 3, 580). Because the CHCl$_3$ used in the decomposition reaction was stabilized with 0.75% EtOH, it is likely that one RNC ligand in the Pt complex was converted to R—NH=C (OEt). FABMS data support this structural characterization for the Pt(p-CN—$C_6H_4$—$C_{10}H_{21}$)(p-C=NH(OEt)—$C_6H_4$—$C_{10}H_{21}$)(CN)$_2$ material. Major molecular ion peaks are observed at 780 (M)$^+$ and 734 (M-EtOH)$^+$ m/e units.

Figure 6A:
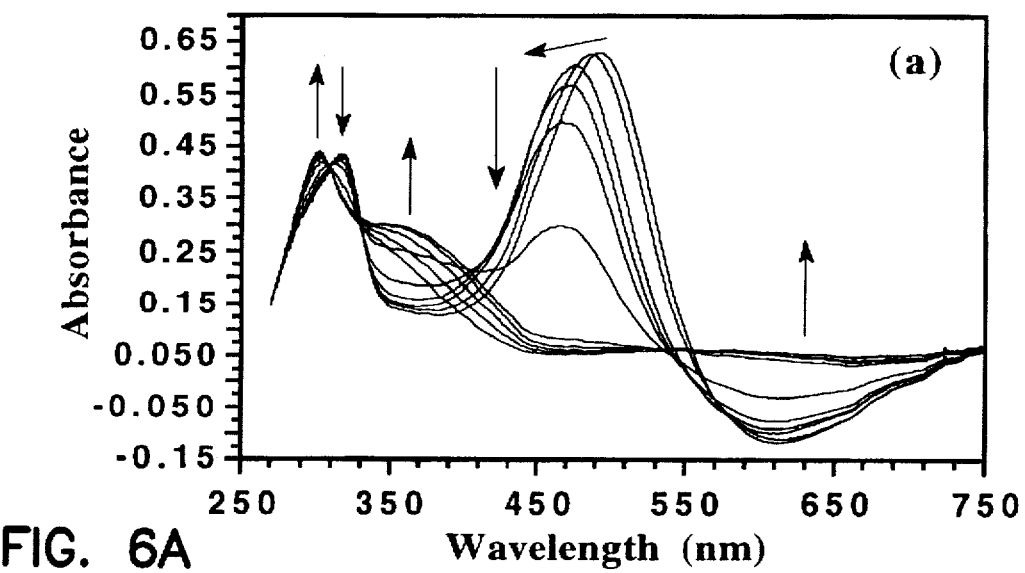
FIG. 6 is a graph of (a) Solid-state absorption spectra of (p-$C_{10}H_{21}$—$C_6H_4$—NC)(p-$C_{10}H_{21}$—$C_6H_4$—NH=C(OEt))Pt(CN)$_2$ dispersed on filter paper upon exposure to $CH_2Cl_2$ vapor. (b) Solid-state electronic emission spectra of (p-$C_{10}H_{21}$—$C_6H_4$—NC)(p-$C_{10}H_{21}$—$C_6H_4$—NH=C(OEt))Pt(CN)$_2$ dry and exposed to $CH_2Cl_2$ vapor.

As Table 4 shows, exposure of a Pt(p-CN—$C_6H_4$—$C_{10}H_{21}$)(p-C=NH(OEt)—$C_6H_4$—$C_{10}H_{21}$)(CN)$_2$ film to VOC vapor results in reversible UV-vis absorption shifts. While the material responds to a small degree to most organic solvent vapor, exposure to CH$_2$Cl$_2$ and CHCl$_3$ result in dramatic absorption maximum shifts from 490 to 350 nm. In FIG. 6a are a sequence of solid state transmission UV-vis absorption spectra showing the time response of a Pt(p-CN—$C_6H_4$—$C_{10}H_{21}$)(p-C=NH(OEt)—$C_6H_4$—$C_{10}H_{21}$) (CN)$_2$ film when exposed to room temperature air saturated with CH$_2$Cl$_2$ vapor. The 490-nm absorption maximum shifts to 472 nm; then the peak intensity decreases, as a new absorption centered at approximately 350 nm grows in. At the same time, the 318-nm band of the dry film isosbestically shifts to 300 nm. This band has previously been assigned to the d$\pi$→p$_z$.$\pi$*(CN) transition in similar complexes (Mason, W. R.; Gray, H. B. *J. Am. Chem.. Soc.* 1968, 90, 5721–5729, ((a) Miskowski, V. M.; Houlding, V. H. *Inorg. Chem.* 1989, 28, 1529–1533. (b) Miskowski, V. M.; Houlding, V. H. *Inorg. Chem.* 1991, 30, 4446–4452). Halogenated solvent vapors appear to strongly perturb any Pt—Pt stacking in the Pt(p-CN—$C_6H_4$—$C_{10}H_{21}$)(p-C=NH(OEt)—$C_6H_4$—$C_{10}H_{21}$)(CN)$_2$ structure, resulting in significant changes in the d$\sigma$*→p$_z$.$\pi$*(CN) transition energy.

Figure 6B:
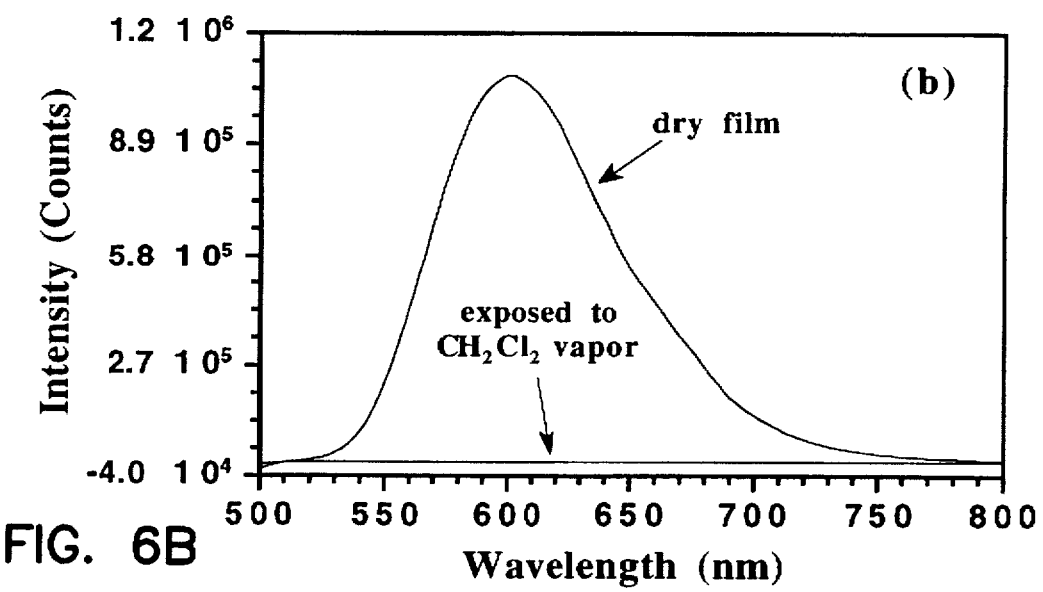

The large difference in absorption maxima of the dry and CH$_2$Cl$_2$ vapor-saturated Pt(p-CN—$C_6H_4$—$C_{10}H_{21}$)(p-C=NH(OEt)—$C_6H_4$—$C_{10}H_{21}$)(CN)$_2$ films may allow for very sensitive VOC detection using molecular luminescence techniques. The dry film shows an intense emission centered at 600 nm upon excitation at 490 nm (see FIG. 6b). The small Stokes shift indicates that this is due to the $^1$(p$_z$.$\pi$* (CN)→d$\sigma$*) fluorescence. The CHCl$_3$-saturated film does not absorb at 490 nm; therefore all emission is due to the dry species. As FIG. 6b shows, exposure of the material to CH$_2$Cl$_2$-saturated air results in an emission band area decrease by a factor of $1.0 \times 10^8$. Considering the spectral background noise (approx. 10 counts) to be negligible, an upper limit for the $CH_2Cl_2$ detection sensitivity can be calculated. Assuming a $CH_2Cl_2$ vapor pressure of 345 torr at 25° C., it would be possible to detect $CH_2Cl_2$ vapor at a 0.005 ppm concentration using the Pt(p-CN—$C_6H_4$—$C_{10}H_{21}$)(p-C≡NH(OEt)—$C_6H_4$—$C_{10}H_{21}$)(CN)$_2$ sensor material.

General Properties of Pt(p-CN—$C_6H_4$—$CH_3$)$_2$(CN)$_2$ and Pt(p-CN—$C_6H_4$—$C_{10}H_{21}$)$_2$(CN)$_2$.

Pt(p-CN—$C_6H_4$—$CH_3$)$_2$(CN)$_2$ is isolated as a bright red microcrystalline solid that is slightly soluble only in halogenated solvents. It can be easily purified by recrystallization from $CH_2Cl_2$/hexanes. No spectral absorbance shifts are observed from Pt(p-CN—$C_6H_4$—$CH_3$)$_2$(CN)$_2$ films upon exposure to VOCs. However, because this compound appears to be much more crystalline than its C10 (decyl) analog, a crystal structure of the Pt(p-CN—$C_6H_4$—$CH_3$)$_2$(CN)$_2$ material may serve as a model for other Pt(CNR)$_2$(CN)$_2$ compounds. Pt(p-CN—$C_6H_4$—$CH_3$)$_2$(CN)$_2$ can be prepared as described above or by heating solid [Pt(CN—$C_6H_4$—$CH_3$)$_4$][Pt(CN)$_4$] to approximately 200° C. This was not the preferred method because of an extra chromatographic purification step required.

Pt(p-CN—$C_6H_4$—$C_{10}H_{21}$)$_2$(CN)$_2$ is isolated as a bright red solid that is at least slightly soluble in most organic solvents. This compound has a sticky amorphous texture similar to that of the Pt(p-CN—$C_6H_4$—$C_{10}H_{21}$)(p-C≡NH(OEt)—$C_6H_4$—$C_{10}H_{21}$)(CN)$_2$ compound. Because of the unusual solubility properties, Pt(p-CN—$C_6H_4$—$C_{10}H_{21}$)$_2$(CN)$_2$ could not be precipitated out of solution for more than a 10-20% recovery, so it was necessary to purify it using column chromatography. However, the increased solubility of Pt(p-CN—$C_6H_4$—$C_{10}H_{21}$)$_2$(CN)$_2$ in organic solvents compared to that for the complex double-salts allow more uniform, consistent films to be cast. The visible absorption maximum (515 nm) is at a slightly longer wavelength than that for Pt(p-CN—$C_6H_4$—$C_{10}H_{21}$)(p-C≡NH(OEt)—$C_6H_4$—$C_{10}H_{21}$)(CN)$_2$ (490 nm). The absence of ethoxy groups (which would not necessarily be coplanar with the Pt(C)$_4$ square plane in the Pt(p-CN—$C_6H_4$—$C_{10}H_{21}$)(p-C≡NH(OEt)—$C_6H_4$—$C_{10}H_{21}$)(CN)$_2$ complex) in the Pt(p-CN—$C_6H_4$—$C_{10}H_{21}$)$_2$(CN)$_2$ compound may allow the material to stack with a smaller Pt—Pt separation than in Pt(p-CN—$C_6H_4$—$C_{10}H_{21}$)(p-C≡NH(OEt)—$C_6H_4$—$C_{10}H_{21}$)(CN)$_2$, lowering the $d\sigma^* \rightarrow p_z\pi^*$(CN) transition energy.

Figure 7:
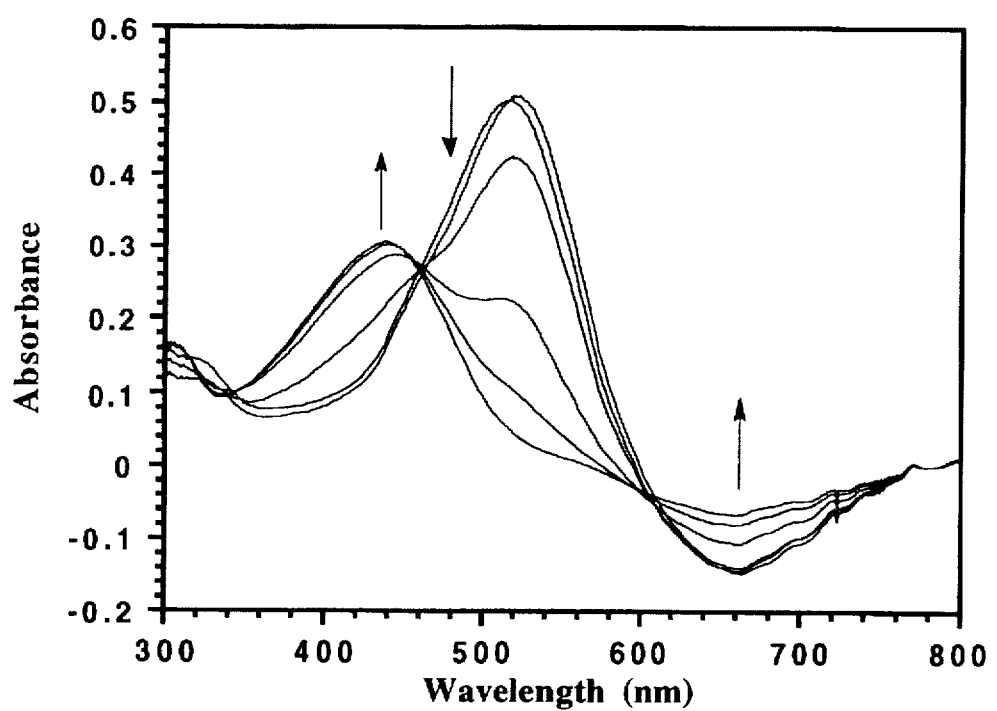
FIG. 7 is a graph of solid-state absorption spectra (transmission mode) of (p-$C_{10}H_{21}$—$C_6H_4$—CN)$_2$Pt(CN)$_2$ dispersed on filter paper. Spectra recorded as air saturated with $CHCl_3$ vapor is admitted into the sample compartment. Spectra are recorded at approximately 1 s intervals. Arrows indicate the direction of change. The negative absorbance at 660 nm is due to light emission from the sample.

As Table 4 shows, exposure of a Pt(p-CN—$C_6H_4$—$C_{10}H_{21}$)$_2$(CN)$_2$ film to VOC vapor results in reversible UV-VIS absorption shifts. No vapochromic shift is observed upon exposure to hexanes, and only small shifts result from exposure to acetone and $CH_3OH$. However, the vapochromic shift increases to 13 nm when VOC=benzene, and exposure to $CH_2Cl_2$ and $CHCl_3$ result in dramatic absorption maximum shifts from 515 to 427 nm. In FIG. 7 are a sequence of solid state transmission UV-vis absorption spectra showing the time response of a Pt(p—CN—$C_6H_4$—$C_{10}H_{21}$)$_2$(CN)$_2$ film when exposed to room temperature air saturated with $CHCl_3$ vapor. The 515-nm absorption maximum shifts to 520 nm; then the peak intensity decreases as a new absorption centered at 427 nm grows in. This process is similar to that for Pt(p-CN—$C_6H_4$—$C_{10}H_{21}$)(p-C≡NH(OEt)—$C_6H_4$—$C_{10}H_{21}$)(CN)$_2$. Again, the Pt—Pt stacking in the Pt(p-CN—$C_6H_4$—$C_{10}H_{21}$)$_2$(CN)$_2$ structure seems to be very sensitive to the presence of halogenated vapor resulting in significant changes in the $d\sigma^* \rightarrow p_z\pi^*$(CN) transition energy. While no systematic electronic emission studies of Pt(p-CN—$C_6H_4$—$C_{10}H_{21}$)$_2$(CN)$_2$ have been done, preliminary observations indicate that the dry material is intensely emissive (as shown in FIG. 7). As with the Pt(p-CN—$C_6H_4$—$C_{10}H_{21}$)(p-C≡NH(OEt)—$C_6H_4$—$C_{10}H_{21}$)(CN)$_2$ material, the large visible vapo-chromic absorption shift in the Pt(p-CN—$C_6H_4$—$C_{10}H_{21}$)$_2$(CN)$_2$ material would allow for extremely sensitive VOC detection using fluorescence spectroscopy (see FIG. 6b for the Pt(p-CN—$C_6H_4$—$C_{10}H_{21}$)(p-C≡NH(OEt)—$C_6H_4$—$C_{10}H_{21}$)(CN)$_2$ fluorescence spectra).

Alkyl chain length has a large effect on the selectivity of vapochromic compounds as well as the degree of shifts observed. Neutral complexes of the form Pt(arylisonitrile)$_2$(CN)$_2$ selectivity towards fewer VOCs than tetrakis double salts, but show enormous vapochromic shifts for the VOCs they detect. The neutral complexes show solubility in some organic solvents, unlike the tetrakis complexes, allowing recrystallization and better characterization via NMR. The tetrakis double salts containing nitro groups in the anion show complex reversibility in vapochromic shifts. Stability among all complexes studied was limited by decomposition of double salts to thermodynamically favored neutral compounds or solubility of neutral complexes in the solvents of test interest with irreversible effects.

Synthesis and general properties of [Pt(phen)p-$C_nH_{2n+1}$—$C_6H_4$—NC)$_2$][Pt(CN)$_4$].

[Pt(phen)(p-$C_nH_{2n+1}$—$C_6H_4$—NC)$_2$][Pt(CN)$_4$] The synthesis of [Pt(phen)(p-$C_{12}H_{25}$—$C_6H_4$—NC)$_2$][Pt(CN)$_4$] is given as a typical example of the complexes of this form, the analogs differing only with alkyl chain length of the isonitrile.

A solution of Pt(phen)Cl$_2$ (25.0 mg, 56.0 mmol) and p-$C_{12}H_{25}$—$C_6H_4$—NC (30.4 mg, 112 mmol) in 25 mL $CH_3CN$ was stirred under Ar atmosphere for 30 min. Solid (tetra n-butyl ammonium)$_2$[Pt(CN)$_4$](68.2 mg, 56.0 mmol) was added to this solution and the mixture was stirred 12 hrs. The solution, originally yellow in color, slowly over time develops a navy blue precipitate. The solid was collected on a medium frit and rinsed with 5 mL acetone. The solid, upon drying overnight in vacuo, yielded a red product in yield 28.6 mg (42%). IR (ATR film): ν(R—NC) 2251, 2236, ν(CN) 2122; UV-Vis (film): $\lambda_{max}$ 518 nm.

[Pt(phen)(p-$C_6H_{13}$—$C_6H_4$—NC)$_2$][Pt(CN)$_4$] This product was a blue solid isolated using the same procedure as described for [Pt(phen)(p-$C_{12}H_{25}$—$C_6H_4$—NC)$_2$][Pt(CN)$_4$]. Yield: 48%; IR (ATR film): ν(R—NC) 2258, 2240, ν(CN) 2122; UV-Vis (film): $\lambda_{max}$ 575 nm.

Significant absorption shifts in the UV-Vis spectra are observed for both [Pt(phen)(p-$C_6H_{13}$—$C_6H_4$—NC)$_2$][Pt(CN)$_4$] and [Pt(phen)(p-$C_{12}H_{25}$—$C_6H_4$—NC)$_2$][Pt(CN)$_4$] upon exposure to various volatile organic solvents; however the vapochromic behavior observed for each compound is quite different. A tabulation of the solvents tested and the observed vapochromic shifts are found in Table 5. The [Pt(Phen)(p-$C_{12}H_{25}$—$C_6H_4$—NC)$_2$][Pt(CN)$_4$] complex showed the largest vapochromic shifts for low molecular weight alcohols (MeOH, EtOH, 1-PrOH, 1-BuOH, amyl alcohol). The fluorinated alcohol $CF_3CH_2OH$ showed the largest vapochromic shift of 55 nm. Longer alkyl chain primary alcohols showed no vapochromic shifts. Other solvents showed less distinct vapochromic changes. The complex [Pt(phen)(p-$C_6H_{13}$—$C_6H_4$—NC)$_2$][Pt(CN)$_4$] showed no vapochromic effects towards water and hexanes. The lack of water sensitivity is highly beneficial to application of these compounds for use in environmental sensors. All vapochiomic shifts observed for this complex were to higher energies upon vapor inclusion and fully reversible upon removal of the solvent vapors.

Figure 8:
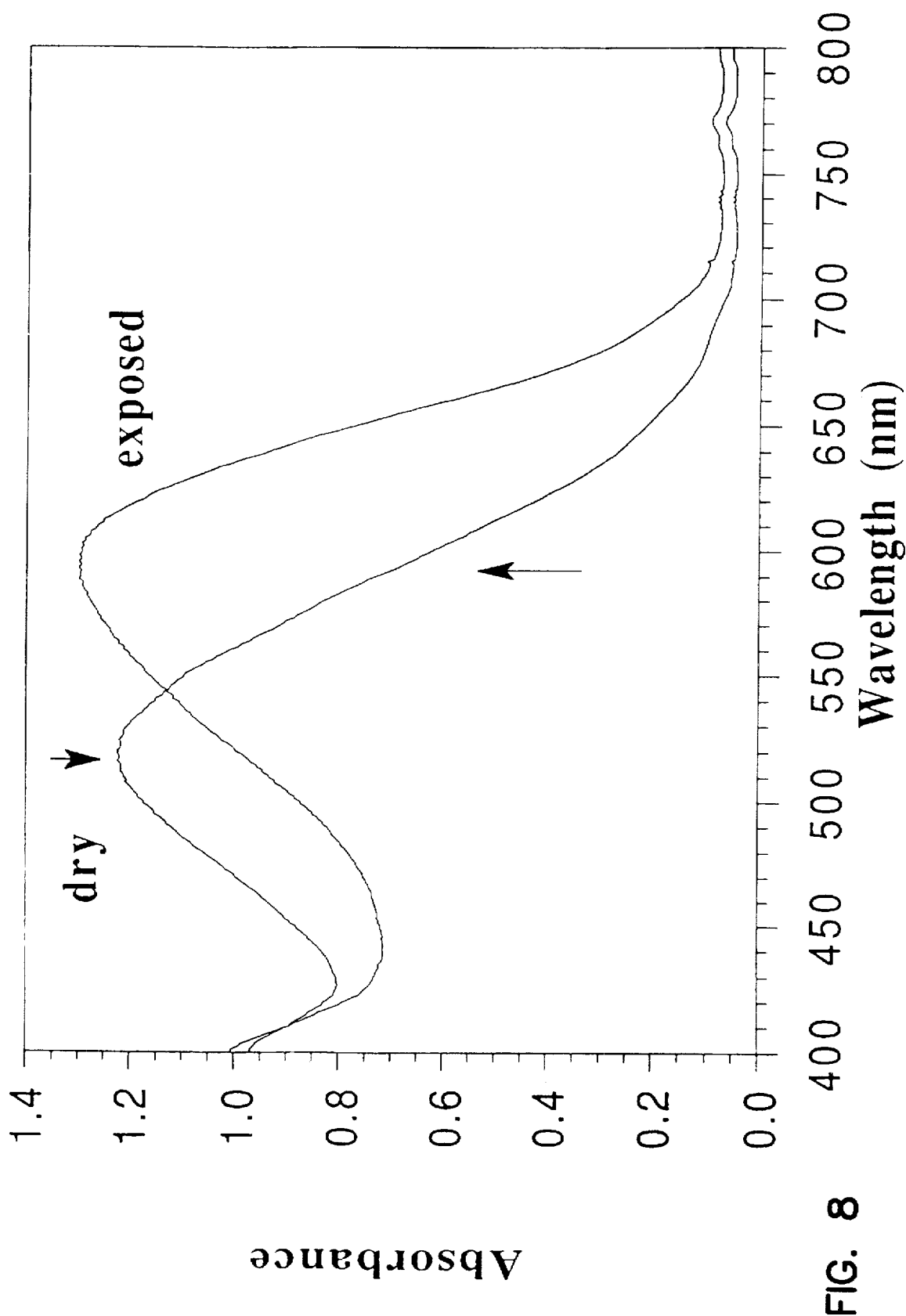
FIG. 8 is a graph of the UV-visible spectra of Pt(phen)(CN—$C_6H_4$—$C_{12}H_{25}$)$_4$][Pt(CN)$_4$] in the absence and presence of dichoromethane vapor.

The [Pt(Phen)(p-$C_{12}H_{25}$—$C_6H_4$—NC)$_2$][Pt(CN)$_4$] compound exhibited even larger vapochromic shifts in the UV-Vis spectra. All shifts observed for this complex were, in contrast with [Pt(phen)(p-$C_6H_{13}$—$C_6H_4$—NC)$_2$][Pt(CN)$_4$], to lower energies. FIG. 8 displays the effect of exposing [Pt(phen)(p-$C_{12}H_{25}$—$C_6H_4$—NC)$_2$][Pt(CN)$_4$] to $CH_2Cl_2$ solvent vapors. A reversible vapochromic shift of 74 nm to lower energy is observed. This corresponds to a visible change of the solid from red to blue. Like the [Pt(phen)(p-$C_6H_{13}$—$C_6H_4$—NC)$_2$][Pt(CN)$_4$] complex, multiple exposure and removal of solvent vapor cycles showed no variation in the fully reversible vapochromic effect observed. As Table 5 indicates, the complex [Pt(phen)(p-$C_{12}H_{25}$—$C_6H_4$—NC)$_2$][Pt(CN)$_4$] showed distinct changes in the 518 nm band for nearly all the solvents tested. Two groups of vapochromic changes, based on the extent of shift, can be constructed based loosely on the functional groups of the organic solvents. Low molecular weight primary alcohols show vapochromic shifts of 30–40 nm to lower energy in all cases observed. Other potentially more toxic organic solvents (including halogenated) have larger vapochromic shifts of 42–74 nm to lower energies. Solvents which induce more diffluse band changes are $Et_2O$ and hexanes. Water shows a slight vapochromic effect for [Pt(phen)(p-$Cl_2H_{25}$—$C_6H_4$—NC)$_2$][Pt(CN)$_4$], but only upon vacuum drying. The reported vapochromic shifts in Table 5 for [Pt(phen)(p-$C_6H_{13}$—$C_6H_4$—NC)$_2$][Pt(CN)$_4$] are all with reference to the compound in air humidity. The range of atmospheric air humidity in which spectra were taken showed no observable differences as a result of water present.

The ATR-IR data for both complexes showed similar behavior in response to solvent vapors to the previously reported tetrakis aryl isonitrile complexes. The main stretching frequencies of interest are the bands corresponding to the coordinated —CN substituents of the anion and the coordinated R—NC substituents of the cation. The frequencies of the isonitrile bands occur at 2258, 2240 cm$^{-1}$ and 2251, 2236 cm$^{-1}$ for the [Pt(phen)(p-$C_6H_{13}$—$C_6H_4$—NC)$_2$][Pt(CN)$_4$] and [Pt(phen)(p-$C_{12}H_{25}$—$C_6H_4$—NC)$_2$][Pt(CN)$_4$] complexes, respectively. These isonitrile bands were invariant upon solvent exposure for the [Pt(phen)(p-$C_6H_{13}$—$C_6H_4$—NC)$_2$][Pt(CN)$_4$] complex. The [Pt(phen)(p-$C_{12}H_{25}$—$C_6H_4$—NC)$_2$][Pt(CN)$_4$] complex did however show some isonitrile band changes upon solvent vapor inclusion. The isonitrile bands of [Pt(phen)(p-$C_{12}H_{25}$—$C_6H_4$—NC)$_2$][Pt(CN)$_4$] shifted reversibly to 2254, 2235 cm$^{-1}$ when exposed to $CH_3CN$, $H_2O$, and MeOH. Exposure of $CHCl_3$ reversibly shifted the isonitrile bands of $C_{12}$(i.e., dodecyl)-PtphenPt to 2259, 2239 cm$^{-1}$. All other solvents tested showed no effect on the isonitrile band of [Pt(phen)(p-$C_{12}H_{25}$—$C_6H_4$—NC)$_2$][Pt(CN)$_4$].

Compounds of the form [Pt(phen)(p-$C_nH_{2n+1}$—$C_6H_4$—NC)$_2$][Pt(CN)$_4$] have been synthesized to discover additional vapochromic compounds. These analogs of the previously studied [Pt(arylisonitrile)$_4$][M(CN)$_4$] (M=Pt, Pd) complexes have been studied to better understand the mechanistic considerations of vapochromism and to find vapochromic complexes exhibiting response to a wide range of VOCs. UV-Vis and ATR-IR data lead to several conclusions:

1. [Pt(phen)(p-$C_nH_{2n+1}$—$C_6H_4$—NC)$_2$][Pt(CN)$_4$] complexes have strong absorptions in the visible region due to electronic transitions characteristic of square planar $d^8$ linear stacking structures.

2. [Pt(phen)(p-$C_nH_{2n+1}$—$C_6H_4$—NC)$_2$][Pt(CN)$_4$] complexes exhibit visible vapochromic changes in response to common VOC vapors. The n=6 alkyl chain length complex shows distinct vapochromic shifts in response primarily to low molecular weight primary alcohols. The n=12 complex responds to a broader range of VOCs, and with larger visible shifts.

3. Alkyl chain length has a profound effect on the vapochromic properties of this series of complexes, both in selectivity of VOC response and the extent of the shifts observed.

4. ATR-IR data suggests that the —CN ligands of the anion may play a role in the vapochromic mechanism, through solvent H-bonding interactions, but other pathways must also be present for inducing the vapochromic effect.

DATA TABLES

TABLE 1

Absorption and Emission $\lambda_{max}$ for Solid-State Films of [Pt(arylisonitrile)$_4$][Pt(CN)$_4$](where arylisonitrile = p-CN—$C_6H_4$—$CnH_{2n+1}$; n = 1, 6, 10, 12, 14)

| n | Absorption Maximum (nm) | Emission Maximum (nm) |
|---|---|---|
| 1 | 744 | 958 |
| 6 | 841 | 910 |
| 10 | 746 | 972 |
| 12 | 764 | 912 |
| 14 | 690 | 876 |

TABLE 2

Absorption and Emission $\lambda_{max}$ and Vapochromic Shifts for Solid-State Films of [Pt(CN—$C_6H_4$—$C_{10}H_{21}$)$_4$][Pt(CN)$_4$]

| Absorption Solvent | | Vapochromic Emission Maximum (nm) | Vapochromic Shift (nm) |
|---|---|---|---|
| none | 746 | 0 | 944 | 0 |
| MeOH | 757 | 11 | 946 | 2 |
| EtOH | 787 | 41 | 992 | 48 |
| 2-PrOH | 782 | 36 | 974 | 30 |
| $Et_2O$ | 787 | 41 | 970 | 26 |
| $CH_3CN$ | 809 | 63 | 980 | 36 |
| hexanes | 775 | 29 | 950 | 6 |
| acetone | 800 | 54 | 986 | 42 |
| benzene | 801 | 55 | 990 | 46 |
| $CH_2Cl_2$ | 811 | 65 | 976 | 32 |
| $CHCl_3$ | 837 | 91 | 1018 | 74 |

*Vapochromic Shift $\lambda_{max}$ (VOC) − $\lambda_{max}$ (none)

TABLE 3

Cyanide CN-Stretching Frequencies and Vapochromic Shifts* Upon Exposure to VOCs for [Pt(CN—$C_6H_4$—$C_{10}H_{21}$)$_4$][Pt(CN)$_4$]

| VOC | v(CN), cm$^{-1}$ | Vapochromic Shift, cm$^{-1}$ |
|---|---|---|
| none | 2125 | — |
| Water | 2125 | 0 |
| Hexanes | 2125 | 0 |
| Carbon $Cl_4$ | 2126 | 1 |
| Diethyl Ether | 2126 | 1 |
| Benzene | 2126 | 1 |
| Acetone | 2126 | 1 |
| Dichloromethane | 2127 | 2 |
| Acetonitrile | 2127 | 2 |
| Chloroform | 2127, 2132 | 2, 7 |
| 2-Propanol | 2128, 2135 | 3, 10 |
| Ethanol | 2128, 2136 | 3, 11 |

TABLE 3-continued

Cyanide CN-Stretching Frequencies and Vapochromic Shifts[a] Upon Exposure to VOCs for [Pt(CN—$C_6H_4$—$C_{10}H_{21}$)$_4$][Pt(CN)$_4$]

| VOC | v(CN), cm$^{-1}$ | Vapochromic Shift, cm$^{-1}$ |
|---|---|---|
| Methanol | 2128, 2138 | 3, 13 |
| 1,1,1-Trifluoroethanol | 2130, 2140 | 5, 15 |

[a]Vapochromic Shift = v(CN)VOC − v(CN)none

TABLE 4

Electronic absorption maxima ($\lambda_{max}$) for solid-state films of the Pt(p-CN—$C_6H_4$—$C_{10}H_{21}$)(p-C=NH(OEt)-$C_6H_4$—$C_{10}H_{21}$)(CN)$_2$ (ORANGE) and Pt(p-CN—$C_6H_4$—$C_{10}H_{21}$)$_2$(CN)$_2$ (RED) materials when exposed to VOCs.[a]

| VOC | ORANGE $\lambda_{max}$ (nm) | ORANGE vapochromic shift (nm)[b] | RED $\lambda_{max}$ (nm) | RED vapochromic shift (nm)[b] |
|---|---|---|---|---|
| none | 490 | — | 515 | — |
| benzene | 490 | 0 | 515 | 0 |
| hexanes | 486 | −4 | 515 | 0 |
| MeOH | 486 | −4 | 512 | −3 |
| $CH_3CN$ | 485 | −5 | 514 | −1 |
| EtOH | 481 | −9 | c | |
| $Et_2O$ | 481 | −9 | 512 | −3 |
| acetone | 479 | −11 | 511 | −4 |
| 2-PrOH | 477 | −13 | c | |
| $CH_2Cl_2$ | 388 | −102 | 430 | −85 |
| $CHCl_3$ | 374 | −116 | 427 | −88 |

[a]The ORANGE material was dispersed on glass, while the RED material was dispersed on filter paper.
[b]Vapochromic shift is $\lambda_{max}$(VOC) − $\lambda_{max}$(none).
[c]Data not collected.

TABLE 5

UV-Vis Absorbance Spectral Data. "Vapochromic" Spectral Shifts Upon Vapor Inclusion

| Solvent | [Pt(phen)($C_6H_{13}$—$C_6H_4$—NC)$_2$][Pt(CN)$_4$] Change (nm) | [Pt(phen)($C_{12}H_{25}$—$C_6H_4$—NC)$_2$][Pt(CN)$_4$] Change (nm) |
|---|---|---|
| $CHCl_3$ | −Δ | +62 |
| $CH_2Cl_2$ | −Δ | +74 |
| $CH_3CN$ | −Δ | +56 |
| acetone | −Δ | +50 |
| benzene | −Δ | +42 |
| $Et_2O$ | −Δ | −Δ |
| THF | −Δ | +58 |
| MeOH | −35 | +38 |
| EtOH | −30 | +38 |
| 1-PrOH | −15 | +40 |
| 1-BuOH | −11 | +40 |
| amyl alcohol | −23 | +34 |
| $CF_3CH_2OH$ | −55 | +30 |
| $H_2O$ | X | X |
| hexanes | X | +Δ |
| $\lambda_{max}$ | 575 (blue) | 518 (red) |

X= no effect
Δ= change in peak shape, not location

The complexes of the present invention may be used alone or in combination with other detection means to analyze or investigate an environment. Other complexes having different response ranges and properties could be used in combination with the complexes of the present invention, for example. Any organic environment, that is any environment where the presence of organic compounds is sought, expected or known to exist may be evaluated according to the practice of this invention, particularly where gaseous organics are known to be present.

What is claimed:

1. A process for indicating the presence of organic vapors comprising the steps of determining the color, absorption or UV, infrared or visible emission spectra of a Pt—Pt double-complex salt of platinum or a neutral platinum complex in the absence of organic vapor, exposing said double-complex salt of platinum or a neutral platinum complex to a gaseous environment, determining the color, absorption or emission spectra of said double-complex salt of platinum or a neutral platinum complex after exposure to said gaseous environment, and comparing the color, absorption and/or emission spectra of said double-complex salt of platinum or a neutral platinum complex in the absence of organic vapor with the color, absorption and/or emission spectra of said double-complex salt of platinum or a neutral platinum complex after exposure to said gaseous environment to determine if there is a difference in the color, absorption and/or emission spectra.

2. The process of claim 1 wherein said double-complex salt is represented by the general formula [Pt(p-CN—$C_6H_4$—$C_nH_{2n+1}$)$_4$][Pt(CN)$_4$], wherein n is a whole positive integer between 1 and 100.

3. The process of claim 2 wherein n is between 1 and 20.

4. The process of claim 1 wherein said double-complex salt is represented by the formula: [Pt(CN—$C_6H_4$-alkyl group)$_4$][Pt(CN)$_4$] where alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

5. The process of claim 1 wherein absorption spectra before exposure to organic vapor and absorption spectra after exposure to organic vapor are measured in the near infrared or infrared regions of the electromagnetic spectrum.

6. The process of claim 1 wherein a change of intensity or position for wavelengths within the spectra is measured.

7. The process of claim 1 wherein said double-complex salt is represented by the general formula [Pt(L)(p-CN—

$C_6H_4$—$C_nH_{2n+1}$)$_2$][Pt(CN)$_4$], wherein n is a whole positive integer between 1 and 100 and L is 1,10-phenanthroline.

8. The process of claim 7 wherein n is between 1 and 20.

9. The process of claim 1 wherein said double-complex salt is represented by the formula: [Pt(L)(CN—$C_6H_4$-alkyl group)$_2$][Pt(CN)$_4$] where L is a 1,10-phenanthroline group or a 2,2'-bipyridine group and where alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

10. The process of claim 1 wherein said double-complex salt is represented by the general formula [Pt(L)(p-CN—$C_6H_4$—$C_nH_{2n+1}$)$_2$][Pt(CN)$_4$], wherein n is a whole positive integer between 1 and 100 and L is an alkyl substituted 1,10-phenanthroline.

11. The process of claim 10 wherein n is between 1 and 20.

12. The process of claim 1 wherein said neutral complex is represented by one of the general formula Pt(p-CN—$C_6H_4$-alkyl group)$_2$(CN)$_2$ or Pt(p-CN—$C_6H_4$-alkyl group)(C(Y)=NH—$C_6H_4$—$C_nH_{2n+1}$)(CN)$_2$, where Y is O—$C_{n'}H_{2n'+1}$ wherein n' is a whole positive integer between 1 and 100 and where alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

13. The process of claim 1 wherein said neutral complex is represented by the general formula Pt(p-CN—$C_6H_4$—$C_nH_{2n+1}$)(C(Y)=NH—$C_6H_4$—$C_nH_{2n+1}$)(CN)$_2$, wherein n is a whole positive integer between 1 and 100 and Y is O—$C_{n'}H_{2n'+1}$ wherein n' is a whole positive integer between 1 and 100.

14. The process of claim 1 wherein said neutral complex is represented by the general formula Pt(p-CN—$C_6H_4$-alkyl group)(C(Y)=NH—$C_6H_4$—$C_nH_{2n+1}$)(CN)$_2$, where Y is O—$C_{n'}H_{2n'+1}$ wherein n' is a whole positive integer between 1 and 100 and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

15. The process of claim 1 wherein said neutral complex is represented by the general formula Pt(p-CN—$C_6H_4$-alkyl group)(C(Y)=NH—$C_6H_4$—$C_nH_{2n+1}$)(CN)$_2$, where Y is O-alkyl group' wherein alkyl group' is a $C_{n'}H_{2n'+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

16. The process of claim 1 wherein said neutral complex is represented by the general formula Pt(p-CN—$C_6H_4$-alkyl group)(C(Y)=NH—$C_6H_4$—$C_nH_{2n+1}$)(CN)$_2$, where Y is NH—$C_nH_{2n'+1}$ wherein n' is a whole positive integer between 1 and 100 and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

17. The process of claim 1 wherein said neutral complex is represented by the general formula Pt(p-CN—$C_6H_4$-alkyl group)(C(Y)=NH—$C_6H_4$—$C_nH_{2n+1}$)(CN)$_2$, where Y is NH-alkyl group' wherein alkyl group' is a $C_nH_{2n'+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

18. The process of claim 1 wherein said neutral complex is represented by the general formula Pt(p-CN—$C_6H_4$-alkyl group)(C(Y)=NH—$C_6H_4$—$C_nH_{2n+1}$)(CN)$_2$, where Y is N—($C_{n'}H_{2n'+1}$)$_2$ wherein n' is a whole positive integer between 1 and 100 and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

19. The process of claim 18 wherein said neutral complex is represented by the general formula Pt(p-CN—$C_6H_4$-alkyl group)(C(Y)=NH—$C_6H_4$—$C_nH_{2n+1}$)(CN)$_2$, where Y is N-(alkyl group)$_2$ wherein alkyl group is a $C_{n'}H_{2n'+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

20. The process of claim 1 wherein said neutral complex is represented by the general formula Pt(p-CN—$C_6H_4$-alkyl group)(C(Y)=NH—$C_6H_4$—$C_nH_{2n+1}$)(CN)$_2$, where Y is N—($C_nH_{2n'+1}$)$_2$ wherein n' is a whole positive integer between 1 and 100 and alkyl group is a CN—$C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

21. The process of claim 1 wherein said double-complex salt is represented by the general formula [Pt(p-CN—$C_6H_4$—$C_nH_{2n+1}$)$_4$][Pt(X)$_4$], wherein n is a positive whole integer between 1 and 100 and X is a complexing ligand for Pt including Cl$^-$, Br$^-$, NO$_2^-$, NCO$^-$, NCS$^-$, or ½ oxalate.

22. The process of claim 1 wherein said double-complex salt is represented by the general formula [Pt(L)(p-CN—$C_6H_4$—$C_nH_{2n+1}$)$_4$][Pt(X)$_4$], wherein L is 1,10-phenanthroline, n is a positive whole integer between 1 and 100 and X is a complexing ligand for Pt including Cl$^-$, Br$^-$, NO$_2^-$, NCO$^-$, NCS$^-$, or ½ oxalate.

23. The process of claim 1 wherein said neutral complex is represented by the general formula Pt(p-CN—$C_6H_4$—$C_nH_{2n+1}$)$_2$(X)$_2$, wherein n is a positive whole integer between 1 and 100 and X is a complexing ligand for Pt including Cl$^-$, Br$^-$, NO$_2^-$, NCO$^-$, NCS$^-$, CN$^-$ or ½ oxalate.

24. A process for indicating the presence of an organic environment comprising the steps of determining the absorption or emission spectra of a Pt—Pt double-complex salt of platinum or a neutral platinum complex in the absence of any organic material other than said salt, exposing said double-complex salt of platinum or a neutral platinum complex to an environment, determining the color, absorption or emission spectra of said double-complex salt of platinum or a neutral platinum complex after exposure to said environment, and comparing the absorption or emission spectra of said double-complex salt of platinum or a neutral platinum complex in the absence of an organic environment with the absorption or emission spectra of said double-complex salt of platinum or a neutral platinum complex after exposure to said environment to determine if there is a difference in the absorption or emission spectra.

25. The process of claim 24 wherein said double-complex salt is represented by the formula: $[Pt(CN-C_6H_4\text{-alkyl group})_4][Pt(CN)_4]$ where alkyl group is a $CN-C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

26. The process of claim 24 wherein absorption spectra before exposure to organic vapor and absorption spectra after exposure to organic vapor are measured in the near infrared or infrared regions of the electromagnetic spectrum.

27. The process of claim 24 wherein a change of intensity or position for wavelengths within the spectra is measured.

28. The process of claim 24 wherein said double-complex salt is represented by the general formula $[Pt(p-CN-C_6H_4-C_nH_{2n+1})_4][Pt(X)_4]$, wherein n is a positive whole integer between 1 and 100 and X is a complexing ligand for Pt.

29. The process of claim 24 wherein said double-complex salt is represented by the formula: $[Pt(L)(CN-C_6H_4\text{-alkyl group})_2][Pt(CN)_4]$ where L is 1,10-phenanthroline and where alkyl group is a $CN-C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

30. The process of claim 24 wherein said double-complex salt is represented by the general formula $[Pt(L)(p-CN-C_6H_4-C_nH_{2n+1})_2][Pt(CN)_4]$, wherein n is a whole positive integer between 1 and 100 and L is an alkyl substituted 1,10-phenanthroline.

31. The process of claim 30 wherein n is between 1 and 20.

32. The process of claim 31 wherein said neutral complex is represented by the general formula $Pt(p-CN-C_6H_4-C_nH_{2n+1})(C(Y)=NH-C_6H_4-C_nH_{2n+1})(CN)_2$, wherein n is a whole positive integer between 1 and 100 and Y is $NH-C_{n'}H_{2n'+1}$ wherein n' is a whole positive integer between 1 and 100.

33. The process of claim 32 wherein n is between 1 and 20.

34. The process of claim 31 wherein said neutral complex is represented by the general formula $Pt(p-CN-C_6H_4\text{-alkyl group})(C(Y)=NH-C_6H_4-C_nH_{2n+1})(X)_2$, wherein n is a positive whole integer between 1 and 100 Y is $O-C_{n'}H_{2n'+1}$ wherein n' is a whole positive integer between 1 and 100 and X is a complexing ligand for Pt including $Cl^-$, $Br^-$, $NO_2^-$, $NCO^-$, $NCS^-$, or ½ oxalate.

35. The process of claim 24 wherein said neutral complex is represented by the general formula $Pt(p-CN-C_6H_4\text{-alkyl group})(C(Y)=NH-C_6H_4-C_nH_{2n+1})(CN)_2$, where Y is $O-C_{n'}H_{2n'+1}$ wherein n' is a whole positive integer between 1 and 100 and alkyl group is a $CN-C_nH_{2+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

36. The process of claim 24 wherein said neutral complex is represented by the general formula $Pt(p-CN-C_6H_4\text{-alkyl group})(C(Y)=NH-C_6H_4-C_nH_{2n+1})(CN)_2$, where Y is $NH-C_{n'}H_{2n'+1}$ wherein n' is a whole positive integer between 1 and 100 and alkyl group is a $CN-C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

37. The process of claim 24 wherein said neutral complex is represented by the general formula $Pt(p-CN-C_6H_4\text{-alkyl group})(C(Y)=NH-C_6H_4-C_nH_{2n+1})(CN)_2$, where Y is N-(alkyl group')$_2$ wherein alkyl group' is a $C_nH_{2n'+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium and alkyl group is a $CN-C_nH_{2n+1}$ alkyl chain where the hydrogen atoms are substituted in part or in whole with substituents selected from the group consisting of alkyl groups of 1 to 100 carbon atoms, halogen atom, hydroxy, cyano, nitro, alkoxy, thio, thioalkyl, and deuterium.

38. The process of claim 24 wherein said double-complex salt is represented by the general formula $[Pt(L)(p-CN-C_6H_4-C_nH_{2n+1})_4][Pt(X)_4]$, wherein L is 1,10-phenanthroline, n is a positive whole integer between 1 and 100 and X is a complexing ligand for Pt including $Cl^-$, $Br^-$, $NO_2^-$, $NCO^-$, $NCS^-$, or ½ oxalate.

39. Double-complex salts represented by the general formulas:
   a) $[Pt(phen)(CN-C_6H_4\text{-alkyl group})_2][PtX_4]$ or b) $[Pt(bpy)(CN-C_6H_4\text{-alkyl group})_2][PtX_4]$ wherein alkyl group comprises an alkyl group of at least 4 carbon atoms and X is selected from the group consisting of $CN^-$, $NO_2^-$, $NCO^-$, $NCS^-$, and ½ oxalate.

40. Neutral platinum complexes comprising platinum complexed by four ligands wherein two ligands are negatively charged groups selected from the group consisting of $CN^-$, $NO_2^-$, $NCO^-$, $NCS^-$, and ½ oxalate and the remaining two ligands are selected from the group of arylisonitrile groups, and a Fisher carbene, with no more than one of said remaining two ligands selected from Fisher carbenes.

* * * * *